United States Patent
Grunze et al.

(10) Patent No.: US 9,080,146 B2
(45) Date of Patent: Jul. 14, 2015

(54) SUBSTRATES CONTAINING POLYPHOSPHAZENE AS MATRICES AND SUBSTRATES CONTAINING POLYPHOSPHAZENE WITH A MICRO-STRUCTURED SURFACE

(75) Inventors: Michael Grunze, Neckargemünd (DE); Ulf Fritz, Hirschhorn (DE)

(73) Assignee: CELONOVA BIOSCIENCES, INC., San Antonio, TX (US)

( * ) Notice: Subject to any disclaimer, the term of this patent is extended or adjusted under 35 U.S.C. 154(b) by 1842 days.

(21) Appl. No.: 12/237,928

(22) Filed: Sep. 25, 2008

(65) Prior Publication Data
US 2009/0117637 A1    May 7, 2009

Related U.S. Application Data

(63) Continuation-in-part of application No. 10/250,985, filed as application No. PCT/EP02/00230 on Jan. 11, 2002, now Pat. No. 8,007,821.

(30) Foreign Application Priority Data

Jan. 11, 2001 (DE) .................... 101 00 961

(51) Int. Cl.
| C09D 185/02 | (2006.01) |
| A61L 27/34 | (2006.01) |
| C12N 5/00 | (2006.01) |
| A61L 27/36 | (2006.01) |
| A61L 27/38 | (2006.01) |
| C08G 79/02 | (2006.01) |

(52) U.S. Cl.
CPC .............. *C12N 5/0068* (2013.01); *A61L 27/34* (2013.01); *A61L 27/3687* (2013.01); *A61L 27/3895* (2013.01); *C08G 79/025* (2013.01); *C09D 185/02* (2013.01); *C12N 2533/30* (2013.01); *C12N 2535/10* (2013.01)

(58) Field of Classification Search
CPC .. C04B 38/0022; C04B 38/045; C04B 35/52; C04B 35/522; C04B 2111/80; C04B 2111/92; A61F 2250/0067; A61F 13/0203; A61F 13/023; A61F 13/42; A61F 2250/0068; A61F 2/0077; A61F 17/11; A61F 17/12022
See application file for complete search history.

(56) References Cited

U.S. PATENT DOCUMENTS

| 3,949,073 A | 4/1976 | Daniels et al. |
| 4,107,288 A | 8/1978 | Oppenheim et al. |
| 4,124,705 A | 11/1978 | Rothman et al. |
| 4,166,800 A | 9/1979 | Fong |
| 4,311,736 A | 1/1982 | Leong |
| 4,318,947 A | 3/1982 | Joung |
| 4,341,844 A | 7/1982 | Leong |
| 4,373,217 A | 2/1983 | Draenert |
| 4,424,208 A | 1/1984 | Wallace et al. |
| 4,424,395 A | 1/1984 | Strom |
| 4,440,750 A | 4/1984 | Glowacki et al. |
| 4,451,647 A | 5/1984 | Allcock et al. |
| 4,452,916 A | 6/1984 | Boschetti |
| 4,480,642 A | 11/1984 | Stoy et al. |
| 4,507,123 A | 3/1985 | Yoshida |
| 4,535,485 A | 8/1985 | Ashman et al. |
| 4,537,916 A | 8/1985 | Bruschtein et al. |
| 4,547,390 A | 10/1985 | Ashman et al. |
| 4,557,764 A | 12/1985 | Chu |
| 4,565,580 A | 1/1986 | Miyata et al. |
| 4,579,880 A | 4/1986 | Ohashi |
| 4,582,640 A | 4/1986 | Smestad et al. |
| 4,592,755 A | 6/1986 | Penton et al. |
| 4,595,713 A | 6/1986 | St. John |
| 4,677,173 A | 6/1987 | Holle et al. |
| 4,698,373 A | 10/1987 | Tateosian et al. |
| 4,728,570 A | 3/1988 | Ashman et al. |
| 4,798,876 A | 1/1989 | Gould et al. |
| 4,803,075 A | 2/1989 | Wallace et al. |
| 4,837,285 A | 6/1989 | Berg et al. |
| 4,849,285 A | 7/1989 | Dillon |
| 4,851,046 A | 7/1989 | Low et al. |
| 4,880,622 A | 11/1989 | Allcock et al. |
| 4,883,699 A | 11/1989 | Aniuk et al. |
| 4,902,511 A | 2/1990 | Kronman |
| 4,911,691 A | 3/1990 | Aniuk et al. |
| 4,912,141 A | 3/1990 | Kronman |
| 4,975,280 A | 12/1990 | Schacht et al. |
| 4,999,188 A | 3/1991 | Solodovnik et al. |
| 5,007,940 A | 4/1991 | Berg |

(Continued)

FOREIGN PATENT DOCUMENTS

| CA | 1252253 | 4/1989 |
| DE | 19613048 A1 | 10/1996 |

(Continued)

OTHER PUBLICATIONS

Allcock, Harry R., "Poly(organophosphazenes-Unusual New High Polymers," Angew. Chem. Int. Ed. Engl. 16, 147-156 (1977).
Caliceti, Paolo, et al., "Polyphosphazene microspheres for insulin delivery," International Journal of Pharmaceutics, 211 (2000) 57-65.
International Search Report and Written Opinion (PCT/US2007/082659, International Searching Authority, 2007.
Kumbar, Sangamesh G., et al., In Vitro and In Vivo Characterization of Biodegradable Poly(organophosphazenes) for Biomedical Applications, Journal of Inorganic and Organometallic Polymers and Materials, vol. 16, No. 4, Dec. 2006, pp. 365-385.
Acta Polymerica 30 (1979), pp. 245-248.
Acta Polymerica 36 (1985), pp. 627-631.
Acta Polymerica 37 (1986) No. 4:203-208.
Allcock, Harry, R., et al., "Antibacterial activity and mutagenicity studies of water-soluble phosphazene high polymers," Biomaterials, vol. 13. No. 2, pp. 857-862 (1992), Butterworth-Heinemann Ltd., USA.

(Continued)

*Primary Examiner* — Debbie K Ware
(74) *Attorney, Agent, or Firm* — Mannava & Kang, P.C.

(57) ABSTRACT

This disclosure relates to substrates containing at least one polyphosphazene with a forming surface as matrices for producing biological materials that can be implanted in a mammal. The disclosure also relates to a method for producing such substrates and substrates containing polyphosphazene with a micro-structured surface.

1 Claim, 8 Drawing Sheets

(56) References Cited

U.S. PATENT DOCUMENTS

| | | |
|---|---|---|
| 5,019,400 A | 5/1991 | Gombotz et al. |
| 5,077,049 A | 12/1991 | Dunn et al. |
| 5,116,387 A | 5/1992 | Berg |
| 5,137,875 A | 8/1992 | Tsunenaga et al. |
| 5,142,008 A | 8/1992 | Holle et al. |
| 5,143,724 A | 9/1992 | Leshchiner et al. |
| 5,158,573 A | 10/1992 | Berg |
| 5,162,430 A | 11/1992 | Rhee et al. |
| 5,204,382 A | 4/1993 | Wallace et al. |
| 5,238,569 A | 8/1993 | Soria et al. |
| 5,258,028 A | 11/1993 | Ersek et al. |
| 5,278,201 A | 1/1994 | Dunn et al. |
| 5,278,202 A | 1/1994 | Dunn et al. |
| 5,292,802 A | 3/1994 | Rhee et al. |
| 5,294,446 A | 3/1994 | Schlameus et al. |
| 5,304,595 A | 4/1994 | Rhee et al. |
| 5,306,500 A | 4/1994 | Rhee et al. |
| 5,308,701 A | 5/1994 | Cohen et al. |
| 5,324,775 A | 6/1994 | Rhee et al. |
| 5,342,557 A | 8/1994 | Kennedy |
| 5,344,452 A | 9/1994 | Lemperle |
| 5,352,715 A | 10/1994 | Wallace et al. |
| 5,368,859 A | 11/1994 | Dunn et al. |
| 5,395,620 A | 3/1995 | Huc et al. |
| 5,397,352 A | 3/1995 | Burres |
| 5,399,351 A | 3/1995 | Leshchiner et al. |
| 5,413,791 A | 5/1995 | Rhee et al. |
| 5,428,024 A | 6/1995 | Chu et al. |
| 5,439,446 A | 8/1995 | Barry |
| 5,446,091 A | 8/1995 | Rhee et al. |
| 5,451,406 A | 9/1995 | Lawin et al. |
| 5,456,693 A | 10/1995 | Conston et al. |
| 5,476,666 A | 12/1995 | Rhee et al. |
| 5,487,390 A | 1/1996 | Cohen et al. |
| 5,487,897 A | 1/1996 | Polson et al. |
| 5,494,673 A | 2/1996 | Andrianov et al. |
| 5,494,682 A | 2/1996 | Cohen et al. |
| 5,500,161 A | 3/1996 | Andrianov et al. |
| 5,510,418 A | 4/1996 | Rhee et al. |
| 5,516,532 A | 5/1996 | Atala et al. |
| 5,529,777 A | 6/1996 | Andrianov et al. |
| 5,548,060 A | 8/1996 | Allcock et al. |
| 5,552,159 A | 9/1996 | Mueller et al. |
| 5,562,099 A | 10/1996 | Cohen et al. |
| 5,562,909 A | 10/1996 | Allcock et al. |
| 5,571,182 A | 11/1996 | Ersek et al. |
| 5,599,852 A | 2/1997 | Scopelianos et al. |
| 5,605,696 A | 2/1997 | Eury et al. |
| 5,624,685 A | 4/1997 | Takahashi et al. |
| 5,633,001 A | 5/1997 | Ågerup |
| 5,634,946 A | 6/1997 | Slepian |
| 5,635,215 A | 6/1997 | Boschetti et al. |
| 5,639,796 A | 6/1997 | Lee |
| 5,648,100 A | 7/1997 | Boschetti et al. |
| 5,681,873 A | 10/1997 | Norton et al. |
| 5,686,425 A | 11/1997 | Lee |
| 5,707,597 A | 1/1998 | Andrianov et al. |
| 5,716,981 A | 2/1998 | Hunter et al. |
| 5,728,752 A | 3/1998 | Scopelianos et al. |
| 5,733,562 A | 3/1998 | Lee |
| 5,752,974 A | 5/1998 | Rhee et al. |
| 5,763,399 A | 6/1998 | Lee |
| 5,776,193 A | 7/1998 | Kwan et al. |
| 5,788,979 A | 8/1998 | Alt et al. |
| 5,792,478 A | 8/1998 | Lawin et al. |
| 5,814,704 A | 9/1998 | Andrianov et al. |
| 5,824,333 A | 10/1998 | Scopelianos et al. |
| 5,840,290 A | 11/1998 | Hench et al. |
| 5,840,819 A | 11/1998 | Biensan |
| 5,843,172 A | 12/1998 | Yang et al. |
| 5,855,895 A | 1/1999 | Andrianov et al. |
| 5,873,904 A | 2/1999 | Ragheb et al. |
| 5,886,026 A | 3/1999 | Hunter et al. |
| 5,914,388 A | 6/1999 | Allcock |
| 5,922,025 A | 7/1999 | Hubbard |
| 5,955,143 A | 9/1999 | Wheatley et al. |
| 5,962,427 A | 10/1999 | Goldstein et al. |
| 5,980,972 A | 11/1999 | Ding |
| 5,997,301 A | 12/1999 | Linden |
| 6,007,573 A | 12/1999 | Wallace et al. |
| 6,015,563 A | 1/2000 | Andrianov et al. |
| 6,063,061 A | 5/2000 | Wallace et al. |
| 6,066,325 A | 5/2000 | Wallace et al. |
| 6,071,530 A | 6/2000 | Polson et al. |
| 6,077,916 A | 6/2000 | Laurencin |
| 6,083,262 A | 7/2000 | Caravel |
| 6,165,489 A | 12/2000 | Berg et al. |
| 6,190,684 B1 | 2/2001 | Hench et al. |
| 6,203,788 B1 | 3/2001 | Blaschuk et al. |
| 6,207,171 B1 | 3/2001 | Payne et al. |
| 6,210,715 B1 | 4/2001 | Starling et al. |
| 6,214,331 B1 | 4/2001 | Vanderhoff et al. |
| 6,235,061 B1 | 5/2001 | Laurencin et al. |
| 6,254,634 B1 | 7/2001 | Anderson |
| 6,261,323 B1 | 7/2001 | Neto |
| 6,261,325 B1 | 7/2001 | de la Mettrie et al. |
| 6,261,573 B1 | 7/2001 | Loebelenz et al. |
| 6,270,748 B1 | 8/2001 | Annan et al. |
| 6,273,913 B1 | 8/2001 | Wright et al. |
| 6,277,392 B1 | 8/2001 | Klein |
| 6,281,015 B1 | 8/2001 | Mooney et al. |
| 6,284,284 B1 | 9/2001 | Naughton |
| 6,290,981 B1 | 9/2001 | Keefer et al. |
| 6,309,420 B1 | 10/2001 | Preissman |
| 6,319,984 B1 | 11/2001 | Song et al. |
| 6,335,028 B1 | 1/2002 | Vogel et al. |
| 6,335,383 B1 | 1/2002 | Scopelianos et al. |
| 6,346,110 B2 | 2/2002 | Wu |
| 6,365,187 B2 | 4/2002 | Mathiowitz et al. |
| 6,383,500 B1 | 5/2002 | Wooley et al. |
| 6,391,343 B1 | 5/2002 | Yen |
| 6,423,332 B1 | 7/2002 | Huxel et al. |
| 6,423,343 B1 | 7/2002 | Lee et al. |
| 6,431,174 B1 | 8/2002 | Knudson et al. |
| 6,432,128 B1 | 8/2002 | Wallace et al. |
| 6,432,437 B1 | 8/2002 | Hubbard |
| 6,436,424 B1 | 8/2002 | Vogel |
| 6,458,387 B1 | 10/2002 | Scott et al. |
| 6,458,889 B1 | 10/2002 | Trollsas et al. |
| 6,485,514 B1 | 11/2002 | Wrenn, Jr. |
| 6,491,903 B1 | 12/2002 | Forster et al. |
| 6,503,556 B2 | 1/2003 | Harish et al. |
| 6,506,411 B2 | 1/2003 | Hunter et al. |
| 6,530,878 B2 | 3/2003 | Silverman et al. |
| 6,531,152 B1 | 3/2003 | Lerner et al. |
| 6,537,574 B1 | 3/2003 | Hubbard |
| 6,544,503 B1 | 4/2003 | Vanderhoff et al. |
| 6,546,936 B2 | 4/2003 | Knudson et al. |
| 6,555,123 B2 | 4/2003 | Williams et al. |
| 6,558,612 B1 | 5/2003 | Hubbard |
| 6,569,195 B2 | 5/2003 | Yang et al. |
| 6,585,994 B2 | 7/2003 | Williams et al. |
| 6,620,185 B2 | 9/2003 | Harvie et al. |
| 6,652,575 B2 | 11/2003 | Wang |
| 6,652,873 B2 | 11/2003 | Deaver et al. |
| 6,660,301 B1 | 12/2003 | Vogel et al. |
| 6,662,805 B2 | 12/2003 | Frondoza et al. |
| 6,666,892 B2 | 12/2003 | Hiles et al. |
| 6,669,719 B2 | 12/2003 | Wallace et al. |
| 6,676,971 B2 | 1/2004 | Goupil et al. |
| 6,680,046 B1 | 1/2004 | Boschetti |
| 6,682,760 B1 | 1/2004 | Noff et al. |
| 6,689,823 B1 | 2/2004 | Bellare et al. |
| 6,699,471 B2 | 3/2004 | Radice et al. |
| 6,713,646 B2 | 3/2004 | Zhang et al. |
| 6,767,637 B2 | 7/2004 | Park et al. |
| 6,790,456 B2 | 9/2004 | Vogel et al. |
| 6,858,634 B2 | 2/2005 | Asrar et al. |
| 6,866,860 B2 | 3/2005 | Nathan |
| 6,869,445 B1 | 3/2005 | Johnson |
| 6,872,799 B2 | 3/2005 | Nathan |
| 6,884,905 B2 | 4/2005 | Zhang et al. |
| 6,916,910 B2 | 7/2005 | Wolfinbarger, Jr. |
| 6,933,326 B1 | 8/2005 | Griffey et al. |

(56) References Cited

U.S. PATENT DOCUMENTS

| | | |
|---|---|---|
| 6,936,271 B1 | 8/2005 | Oliver et al. |
| 6,949,251 B2 | 9/2005 | Dalal et al. |
| 6,962,979 B1 | 11/2005 | Rhee |
| 6,967,234 B2 | 11/2005 | Nathan |
| 7,004,977 B2 | 2/2006 | Ashman |
| 7,012,126 B2 | 3/2006 | Matsuda et al. |
| 7,025,980 B1 | 4/2006 | Williams et al. |
| 7,025,990 B2 | 4/2006 | Sawhney |
| 7,026,374 B2 | 4/2006 | Nathan et al. |
| 7,053,134 B2 | 5/2006 | Baldwin et al. |
| 7,053,209 B1 | 5/2006 | Gibson et al. |
| 7,056,277 B2 | 6/2006 | Silverman et al. |
| 7,057,019 B2 | 6/2006 | Pathak |
| 7,060,287 B1 | 6/2006 | Hubbard et al. |
| 7,060,298 B2 | 6/2006 | Vogel et al. |
| 7,077,144 B2 | 7/2006 | Knudson et al. |
| 7,094,369 B2 | 8/2006 | Buiser et al. |
| 7,129,209 B2 | 10/2006 | Rhee |
| 7,131,997 B2 | 11/2006 | Bourne et al. |
| 7,135,593 B2 | 11/2006 | Zhang et al. |
| 7,144,414 B2 | 12/2006 | Harvie et al. |
| 7,157,080 B2 | 1/2007 | Radice et al. |
| 7,160,931 B2 | 1/2007 | Cheng et al. |
| 7,192,984 B2 | 3/2007 | Berg et al. |
| 7,244,270 B2 | 7/2007 | Lesh |
| 7,249,601 B2 | 7/2007 | Silverman et al. |
| 7,265,199 B2 | 9/2007 | Grunze |
| 7,288,319 B2 | 10/2007 | Baldwin et al. |
| 7,303,756 B1 | 12/2007 | Bodmeier |
| 7,314,636 B2 | 1/2008 | Caseres et al. |
| 7,326,172 B2 | 2/2008 | Miller |
| 7,338,657 B2 | 3/2008 | Vogel et al. |
| 7,922,764 B2 * | 4/2011 | Gordy et al. ............... 623/2.42 |
| 8,007,821 B2 * | 8/2011 | Grunze ....................... 424/423 |
| 2001/0014717 A1 | 8/2001 | Hossainy et al. |
| 2001/0027340 A1 | 10/2001 | Wright et al. |
| 2001/0029351 A1 | 10/2001 | Falotico et al. |
| 2002/0005206 A1 | 1/2002 | Faletico et al. |
| 2002/0016637 A1 | 2/2002 | Anton |
| 2002/0051730 A1 | 5/2002 | Bodnar et al. |
| 2002/0068089 A1 | 6/2002 | Vogel et al. |
| 2002/0094440 A1 | 7/2002 | Llanos et al. |
| 2002/0111590 A1 | 8/2002 | Davila et al. |
| 2002/0119202 A1 | 8/2002 | Hunter et al. |
| 2002/0133183 A1 | 9/2002 | Lentz et al. |
| 2002/0143386 A1 | 10/2002 | Davila et al. |
| 2002/0151466 A1 | 10/2002 | Hubbard et al. |
| 2002/0165608 A1 | 11/2002 | Llanos et al. |
| 2002/0197326 A1 | 12/2002 | Vogel et al. |
| 2003/0004568 A1 | 1/2003 | Ken et al. |
| 2003/0060877 A1 | 3/2003 | Falotico et al. |
| 2003/0065345 A1 | 4/2003 | Weadock |
| 2003/0065377 A1 | 4/2003 | Davila et al. |
| 2003/0099683 A1 | 5/2003 | Grunze |
| 2003/0140930 A1 | 7/2003 | Knudson et al. |
| 2003/0149490 A1 | 8/2003 | Ashman |
| 2003/0153806 A1 | 8/2003 | Miller |
| 2003/0153983 A1 | 8/2003 | Miller et al. |
| 2003/0153985 A1 | 8/2003 | Lee |
| 2003/0157142 A1 | 8/2003 | Nagel et al. |
| 2003/0171646 A1 | 9/2003 | Pratt et al. |
| 2003/0215519 A1 | 11/2003 | Schwartz et al. |
| 2004/0014936 A1 | 1/2004 | Grunze et al. |
| 2004/0020497 A1 | 2/2004 | Knudson et al. |
| 2004/0028676 A1 | 2/2004 | Klein et al. |
| 2004/0047892 A1 | 3/2004 | Desrosiers et al. |
| 2004/0091425 A1 | 5/2004 | Boschetti |
| 2004/0096514 A1 | 5/2004 | Vogel et al. |
| 2004/0096969 A1 | 5/2004 | Grunze |
| 2004/0117033 A1 | 6/2004 | Frondoza et al. |
| 2004/0142465 A1 | 7/2004 | Radice et al. |
| 2004/0185021 A1 | 9/2004 | Hubbard |
| 2004/0187878 A1 | 9/2004 | Knudson et al. |
| 2004/0210230 A1 | 10/2004 | Furlow |
| 2004/0241203 A1 | 12/2004 | Shakesheff et al. |
| 2005/0025708 A1 | 2/2005 | Vogel et al. |
| 2005/0037047 A1 | 2/2005 | Song |
| 2005/0136093 A1 | 6/2005 | Denk |
| 2005/0165203 A1 | 7/2005 | Kohn et al. |
| 2005/0208095 A1 | 9/2005 | Hunter et al. |
| 2005/0209629 A1 | 9/2005 | Kerr et al. |
| 2005/0234210 A1 | 10/2005 | Andrianov et al. |
| 2006/0008529 A1 | 1/2006 | Meyerhoff et al. |
| 2006/0067883 A1 | 3/2006 | Krom et al. |
| 2006/0088476 A1 | 4/2006 | Harder et al. |
| 2006/0147895 A1 | 7/2006 | Purdum |
| 2006/0201673 A1 | 9/2006 | Welton et al. |
| 2006/0240064 A9 | 10/2006 | Hunter et al. |
| 2006/0246109 A1 | 11/2006 | Hossainy et al. |
| 2006/0251582 A1 | 11/2006 | Reb |
| 2006/0251697 A1 | 11/2006 | Li |
| 2007/0003503 A1 | 1/2007 | Sabetsky |
| 2007/0003584 A1 | 1/2007 | Anderson |
| 2007/0077544 A1 | 4/2007 | Lemperle et al. |
| 2007/0100449 A1 | 5/2007 | O'Neil et al. |
| 2007/0191964 A1 | 8/2007 | Preissman |
| 2007/0240725 A1 | 10/2007 | McKay |
| 2007/0292429 A1 | 12/2007 | Brady et al. |
| 2008/0003256 A1 | 1/2008 | Martens et al. |
| 2008/0015498 A1 | 1/2008 | Lesh |
| 2008/0058954 A1 | 3/2008 | Trieu |
| 2008/0095816 A1 | 4/2008 | Gordy et al. |
| 2008/0102029 A1 | 5/2008 | Fritz et al. |

FOREIGN PATENT DOCUMENTS

| | | |
|---|---|---|
| DE | 19613048 C2 | 10/1996 |
| DE | 19744135 C1 | 3/1999 |
| DE | 10019982 A1 | 10/2001 |
| DE | 10100961 A1 | 8/2002 |
| EP | 0150699 A2 | 8/1985 |
| EP | 0286709 A1 | 10/1988 |
| EP | 0706376 B1 | 6/1997 |
| EP | 0804909 A2 | 11/1997 |
| EP | 0970711 A2 | 1/2000 |
| EP | 1112094 B1 | 7/2001 |
| EP | 1179353 A1 | 2/2002 |
| EP | 1337285 A1 | 8/2003 |
| EP | 1426075 A2 | 6/2004 |
| EP | 0970711 B1 | 10/2004 |
| EP | 1488817 A1 | 12/2004 |
| JP | 58079915 A | 5/1983 |
| JP | 62086024 A2 | 4/1987 |
| JP | 4337328 A | 11/1992 |
| JP | 7082279 A2 | 3/1995 |
| WO | WO 8809664 A1 | 12/1988 |
| WO | WO 9321858 A1 | 11/1993 |
| WO | WO 9502628 A1 | 1/1995 |
| WO | WO 9528150 A | 10/1995 |
| WO | WO 9528966 A1 | 11/1995 |
| WO | WO 9600103 A1 | 1/1996 |
| WO | WO 9604015 A1 | 2/1996 |
| WO | WO 9625176 A1 | 8/1996 |
| WO | WO 9625897 A2 | 8/1996 |
| WO | WO 9629059 A1 | 9/1996 |
| WO | WO 9800531 A | 1/1998 |
| WO | WO 9831734 A1 | 7/1998 |
| WO | WO 9843618 A2 | 10/1998 |
| WO | WO 9852605 A1 | 11/1998 |
| WO | WO 9856312 A1 | 12/1998 |
| WO | WO 9909088 A2 | 2/1999 |
| WO | WO 9916416 A2 | 4/1999 |
| WO | WO 9916477 A2 | 4/1999 |
| WO | WO 9916477 A3 | 4/1999 |
| WO | WO 9942147 A1 | 8/1999 |
| WO | WO 9952356 A1 | 10/1999 |
| WO | WO 0032238 | 6/2000 |
| WO | WO 0056254 A | 9/2000 |
| WO | WO 0061204 A1 | 10/2000 |
| WO | WO 0136008 A2 | 5/2001 |
| WO | WO 0136008 A3 | 5/2001 |
| WO | WO 0145763 A1 | 6/2001 |
| WO | WO 0149340 A1 | 7/2001 |
| WO | WO 0170296 A1 | 9/2001 |

(56) References Cited

FOREIGN PATENT DOCUMENTS

| WO | WO 0172281 A2 | 10/2001 |
|---|---|---|
| WO | WO 01/80919 A2 | 11/2001 |
| WO | WO 01/80919 A3 | 11/2001 |
| WO | WO 0180919 A2 | 11/2001 |
| WO | WO 0187368 A1 | 11/2001 |
| WO | WO 0187372 A1 | 11/2001 |
| WO | WO 0213882 A1 | 2/2002 |
| WO | WO 0224247 A1 | 3/2002 |
| WO | WO 02/064666 A2 | 8/2002 |
| WO | WO 02/064666 A3 | 8/2002 |
| WO | WO 02077073 A2 | 10/2002 |
| WO | WO 03015719 A | 2/2003 |
| WO | WO 2004004795 A | 1/2004 |
| WO | WO 2004011055 A2 | 2/2004 |
| WO | WO 2004048432 A | 6/2004 |
| WO | WO 2004060283 A2 | 7/2004 |
| WO | WO 2006046155 A2 | 5/2006 |
| WO | WO 2007056316 A2 | 5/2007 |

OTHER PUBLICATIONS

Allcock, H., "Phosphazene high polymers with bioactive substitutent groups: prospective anesthetic aminophosphazenes," Macromolecules, 15(3):689-693 (1982).
Ambrosio, et al., "Novel Polyphosphazene-Hydroxyapatite Composites as Biomaterials," IEE Engineering in Medicine and Biology Magazine, Sep./Oct. 2003, pp. 18-26.
Barrett, Eric W., "Patterning Poly(organophosphazenes) for Selective Cell Adhesion Applications," Biomacromolecules, (2005), 6, 1689-1697.
Barrett, Eric W., "Polyphosphazenes for Biomedical Devices and Other Applications," Ph.D. Thesis in Chemistry, Pennsylvania State University, Dec. 2005.
Chaikof, Elliott L., "The Development Prosthetic Heart Valves—Lessons in Form and Function," Oct. 4, 2007, vol. 357:1368-1371, No. 14.
Champion, J., et al., "Particle shape: A new design parameter for micro- and nanoscale drug delivery carriers," Journal of Controlled Release, 121 (2007) 3-9.
Chaubal, M., et al., "Polyphosphates and other phosphorus-containing polymers for drug delivery applications," Critical Reviews™ in Therapeutic Drug Carrier Systems, 20(4):295-315 (2003).
Cohen, Smadar, et al., "Design of Synthetic Polymeric Structures for Cell Transplantation and Tissue Engineering," Clinical Materials, vol. 13, 3-10 (1993), Elsevier Science Publishers Ltd., England.
Contreras, Miguel Angel, et al., "Temperature coefficients of peptides dissolved in hexafluoroisopropanol monitor distortions of helices," Letters in Peptide Science, 4 (1979) 29-39.
Cui, et al., "Preparation of Controlled Releasing Acrylic Polymer Microspheres of Acebutolol Hydrochloride and Those Powder Coated Microspheres with Sodium Alginate in a Polymeric Spherical Crystallization System," Che. Phar. Bull., (1990), vol. 44, No. 4, pp. 837-842.
De Jaeger, Roger, et al., "Poly(organophosphazene)s and Related Compounds: Synthesis, Properties and Applications," Prog. Polym. Sci., vol. 23, 179-276 (1998), Pergamon Press, Great Britain.
De Scheerder, Ivan K., et al., "Angiopeptin Loaded Stents Inhibit the Neointimal Reaction Induced by Polymer Coated Stents Implanted in Porcine Coronary Arteries," Abstract 772-6, pp. 286A, JACC (Feb. 1995). (Abstract).
El-Amin, et al., "The Biocompatibility of Biodegradable Glycine Containing Polyphosphazenes: A Comparative Study in Bone," Journal of Inorganic and Organometallic Polymers and Materials, 2006, vol. 16, No. 4, pp. 387-396.
Gast, Klaus, et al., "Fluoroalcohol-induced structural changes of proetins: some aspects of cosolvent-protein interactins," Eur Biophys J (2001) 20: 273-283.
Goedemoed, J., et al., "Development of implantable antitumor devices based on polyphosphazenes," Die Makromolekulare Chemie, 19:341-365 (1988).
Grunze, Michael, et al., 32P-labeled polyphosphazenes, 1999, Chemical Abstracts, vol. 130, No. 20: 272061.
Guigley, Kevin S., "Hydrogen Bonded Polymer Blends," Ph.D. Thesis in Materials Science and Engineering, Pennsylvania State Univerfsity, Dec. 2001.
Hansen, Charles M., "Hansen Solubility Parameter—A User's Handbook," 2000 by CRC Press LLC.
Henry, R., et al., "Topical lidocaine-prilocaine spray for the treatment of premature ejaculation," International Journal of Impotence Research, 15(4):277-281 (2003).
Honarkar, Hengameh, et al., "Applications of inorganic Polymeric Materials, III: Polyphosphazenes," Monatshefte fur Chemie 138, 923-933 (2007).
Hori, Yoshio, et al., "Functional Analysis of the Tissue-Engineered Stomach Wall," Artificial Organs, 2002, 26 (10):868-893, Blackwell Publishing, Inc., International Society for Artificial Organs.
Huang, Yangmin, et al., "Long-term biocompatability evaluation of a novel polymer-coated sent in a porcine coronary stent model," Therapy and prevention, 2003, Coronary Artery Disease, vol. 14, No. 5, 401-408.
Ibim, Sobrasua M., et al., "Controlled Macromolecule Release from Poly(phosphazene) Matrices," Journal of Controlled Release, vol. 40, 31-39 (Jun. 1996), Elsevier Science B.V.
International Search Report and Written Opinion (PCT/US2007/082426), International Searching Authority, 2007.
International Search Report and Written Opinion (PCT/US2007/082430), International Searching Authority, 2007.
International Search Report and Written Opinion (PCT/US2007/082651), International Searching Authority, 2007.
International Search Report and Written Opinion (PCT/US2007/082672), International Searching Authority, 2007.
International Search Report and Written Opinion (PCT/US2007/083199), International Searching Authority, 2007.
International Search Report and Written Opinion (PCT/US2007/083209), International Searching Authority, 2007.
International Search Report and Written Opinion (PCT/US2007/083043), International Searching Authority, 2007.
International Search Report and Written Opinion (PCT/US2007/083216), International Searching Authority, 2007.
Jayakrishnan, et al., "Hydrogel microspheres from crosslinked poly(methyl methacrylate): synthesis and biocompatibility studies," Bull. Mater. Sci., Mar. 1989, vol. 12, No. 1, pp. 17-25.
Kajiwara, M., "The Study of the Cultivaton of Chinese Hamster Ovary and Bows Cell Lines," Phosphorus, Sulfur, and Silicon, vol. 76, pp. 163-166 (1993), Gordon and Breach Science Publishes S.A., USA.
Kingshott, P., "Surfaces that Resist Bioadhesion," Current Opinion in Solid State and Materials Science, vol. 4, 403-412 (1999), Pergamon.
Kumar, Yogesh, et al., "Influence of Fluoro. Chloro and Alkyl Alcohols on the Folding Pathway of Human Serum Alubmin," J. Biochem., (2005), 138, 335-341.
Kumar, Yogesh, et al., "Molten-globule like partially folded states of human serum albumin induced by fluoro and alkyl alcohols at low pH," Archives of Biochemistry and Biophysics, 426 (2004) 3-10.
Laurencin, Cato T., et al., "use of polyphosphazenes for skeletal tissue regeneratin," J. Biomedical Maerials Research, vol. 27, No. 7, pp. 963-973 (1993), John Wiley & Sons, Inc., USA.
Laurencin, C. et al., "Controlled release using a new bioerodible polyphosphazene matrix system," Journal of Biomedical Materials Research, 21:1231-1246 (1987).
Lemmouchi, Y., et al., "Biodegradable Polyphosphazenes for Drug Delivery," Macromolecular Symposia, vol. 123, 103-112 (Sep. 1997) Wiley VCH, Weinheim, Germany.
Lopez, Gabriel P., et al., "Glow Discharge Plasma Deposition of Tetraethylene Glycol Dimethyl Ether for Fouling-Resistant Biomaterial Surfaces," J. of Biomedical Materials Research, vol. 26, 415-439 (1992), John Wiley & Sons, Inc., USA.
Macromolecules 1987, vol. 20, pp. 782-789.
Maher, Andrew Elessar, "Synthesis and Characterization of Mixed-Substitutent Poly(Organophosphazenes)," Ph.D. Thesis in Chemistry, Pennsylvania State University, May 2004.

(56) References Cited

OTHER PUBLICATIONS

"Making Better Magnetic Nanoparticles," Physorg.com, Science:Physics: Tech:nano:news; Source: National Cancer Institute, Dec. 18, 2006.

Mark, James E., et al., "Polyphosphazenes", Inorganic Polymers, 1992, pp. 61-139, XP000866367, pp. 95-117.

McCaffrey, R.R. et al., "Synthesis, Casting, and Diffusion Testing of Poly[bis(tri-fluoroethoxy)phosphazene] Membranes," J. of Membrane Science, vol. 28, 47-67 (1986), Elsevier Science Publishers B.V., Netherlands.

Mrowietz, C., et al., "Haemocompatibility of polymer-coatd stainless steel stents as compared to uncoated stents," Clinical Hemorheology and Microcirculation, 32 (2005) 89-103.

Nielsen, Gunmar D., et al., "Sensory irritation mechanisms investigated from model compounds: trifluoroethanol, hexafluoroisopropanol and methyl hexafluoroisopropyl ether," 1996, Arch Toxicol, 70:319-328.

Phadke, et al.,"Embolization of Cranial/Spinal Tumors and Vascular Malformations with Hydrogel microspheres," Acta Radiologica, 2002, vol. 43, pp. 15-20.

Ph. Potin & R. DeJaeger, "Review: Polyphosphazenes: Synthesis, Structures, Properties, Applications," European Polymer Journal, vol. 27, 341-348 (1991), Pergamon Press, Great Britain.

Rao, et al., "Hydrolysed Microspheres From Cross-Linked Polymethyl Methacrylate (Hydrogel)", J. Neuroradiol, 1991, vol. 18, pp. 61-69.

Reichert, W. M., et al., "Polyphosphazenes: Effect of molecular motions on thrombogenesis," Journal of Biomedical Materials Rsearch, (1982), vol. 16, 301-312.

Richter, Goetz M., et al., "A New Polymer Concept for Coating of Vascular Stents using PTFEP (poly(bis(trifluoroethoxy)phosphazene) to Reduce Thrombogenicity and Late In-Stent Stenosis," Investigative Radiology, Apr. 2005, vol. 40, No. 4, 210-218.

Roccatano, Danilo, et al., "Effect of hexafluoroisopropanol alcohol on the structure of melittin: A molecular dynamics simulation study," Protein Science, 2005, 14:2582-2589.

Rothemund, Sven, et al., "Temperature coefficients of amide proton NMR resonance frequencies in trifluoroethanol: A monitor of intramolecular hydrogen bonds in helical peptides?" Journal of Biomecular NMR, 8 (1996) 93-97.

Rupp, Frank, et al., "Initials Biofilm Formations by Dynamic Protein Interactions at Surface-Modified Titanium Implants," BIOmaterialien, Apr. 2003.

Steely, Lee Brent, "Hydrophobic and Hydrophilic Conrol in Polyphosphazene Materials," Ph.D. Thesis in Chemistry, Pennsylvania State University, Aug. 2007.

Thanoo, et al., "Preparation of Hydrogel Beads from Crosslinked Poly(Methyl Methacrylate) Microspheres by Alkaline Hydrolysis," J. Appl. P. Sci., vol. 39, pp. 1153-1161 (1990) (abstract only).

Veronese, Francesco M., et al., "Polyphosphazene Membranes and Microspheres in Periodontal Diseases and Implant Surgery," Biomaterials, vol. 20, 91-98 (1999), Elsevier, USA.

Vinogradova, S.V., et al., "Open-chain Poly(organophosphazenes). Synthesis and Properties," Russian Chemical Reviews, vol. 67, 515-534 (1998), Russian Academy of Sciences and Turpion Ltd.

Waksman, R., "Vasvular Brachytherapy: Applications in the Era of Drug-Eluting Stents," reviews in Cardiovascular Medicine, vol. 3, S23-S30 (2002), Medreviews, LLC, USA.

Welle, A., et al., "Plasma Protein Adsorption and Platelet Adhesion on Poly[bis(trifluoroethoxy)phosphazene] and reference material surfaces," appeared in J. Colloid Intef. Sci., 197, 263-274, (1998).

Welle, A., et al., "Polyphosphazenes as antithrombotic coatings for prostetic heart elves," Presented at 19th Annual Meeting of the Adhesion Society, Myrtle Beach, SC, 4 pages (Feb. 1996).

Welle, Alexander, et al., "Blood Compatibility of Poly[bis(trifluoroethoxy)phosphazene]," Institute of Applied Physical Chemistry, JAMP, vol. 4, 6-10, (2000), University of Heidelberg, Germany.

Welle, Alexander, "Competitive plasma protein adsorption on modified polymer surfaces monitored by quartz crystal microbalance technique," J. Biomater. Sci. Polymer Edn. (2004) vol. 15, No. 3, pp. 357-370.

Welna, Daniel Thomas, "Design, Synthesis, and Characterization of Polymeric Materials for uses in Energy Storage Applications," Ph.D. Thesis in Chemistry, Pennsylvania State University, Aug. 2006.

Yao, Shenggen, et al., "Peptide self-association in aqueous trifluoroethanol monitored by pulsed field gradient NMR diffusion measurements," Journal of Biomolecular NMR, 16:109-111, 2000.

Zeifang, Felix, et al., "Improved osseointegration of PTFEP-coated titanium implants," Med Sci Monit, 2008; 14(2): BR35-40, PMID: 18227757.

Zeifang, Felix, et al., "Method of non-destructive mechanical testing of new surface coatings for prostheses," Biomed Tech 2006; 51:3-7.

* cited by examiner

SUBSTRATES CONTAINING POLYPHOSPHAZENE AS MATRICES AND SUBSTRATES CONTAINING POLYPHOSPHAZENE WITH A MICRO-STRUCTURED SURFACE

CROSS-REFERENCE TO RELATED APPLICATIONS

This application is a continuation-in-part of U.S. patent application Ser. No. 10/250,985, of which is now U.S. Pat. No. 8,007,821 which is a 35 U.S.C. §371 National Stage filing application of PCT Application No. PCT/EP02/00230, filed Jan. 11, 2002, which claims priority to German patent No. DE 101 00 961.5, filed Jan. 11, 2001, the entire disclosures of which are incorporated herein by reference.

FIELD OF THE INVENTION

This disclosure relates to substrates and to methods for producing substrates that have utility as matrices or surfaces for producing biological materials that can be implanted in mammals.

BACKGROUND OF THE INVENTION

Culturing of cells, especially endothelial cells, with the goal of growing artificial organs is an important development in implantology. One particular advantage of this technology is that implants prepared in this manner are expected to exhibit complete compatibility with the body. Because cell collections cultured ex vivo initially do not have either the shape or the mechanical stability desired for the later implants such as organs, arteries, and the like, such implants can be initially preformed on a form-building or "forming" substrate on which cells are cultured. These form-building substrates can serve as primary supporting structures or supporting substrates on which cells are cultured and developed.

Examples of form-building substrates that have been studied as possible primary supporting structures for such implant formation include polylactides, polyethylene glycols, polyurethanes, polytetrafluoroethylene (PTFE or Teflon®), and inorganic substrates, as well as more common materials such as polyurethanes, polyethylenes, and polypropylenes. Other potential materials included hydrolyzed polyacrylonitrile, hydrophilic polyethers, diacrylates, an expandable shell of epsilon-PTFE, and various hydrogels. This group of potentially applicable materials can also be supplemented by polyvinylpyrrolidone (PVP), polyvinyl alcohols (PVA), polyethylene oxide (PEO), and polyhydroxyethyl methacrylate p(HEMA). Examples of form-building substrates which are supporting structures for cell cultures have been disclosed, for example, in WO 98/56312, WO 96/00103, EP-A-0 810 845, U.S. Pat. Nos. 4,883,699, 4,911,691, 4,480,642, 4,798, 876, 4,424,395, and EP-A-0 804 909, the entire disclosures of which are incorporated herein by reference.

Because the inherent properties of these materials are unique, each of these potential substrates exhibits characteristics that make them more or less useful for certain applications in the culture of artificial implants. Similarly, these materials also have certain undesirable properties, such as limited blood or tissue compatibility, difficulty in preparing or processing the material, difficulty in fabricating the supporting substrate itself excessive porosity that leads to strong cell adhesion and results in damage when separating the cultured cell material from the supporting substrate. Other materials may require the addition of plasticizers to achieve the desired properties, which can reduce compatibility with the blood and various cells and tissues.

Accordingly, there is a need to develop substrate materials that can serve as form-building or "forming" substrates, on which cells can be cultured. There is also a need to understand and develop substrate materials as matrices for producing biological materials that can be implanted in a mammal. There is also a need to be able to control the degree or extent of cellular adhesion at or on a substrate, for example within, around, and at the interfacial boundary contacting an implant.

BRIEF SUMMARY OF THE INVENTION

The present disclosure relates to substrates containing a polyphosphazene with a form-building or forming surface, which are utilized as matrices for producing biological materials that can be implanted in a mammal. This disclosure also describes a process for producing such substrates, substrates containing polyphosphazene with micro-structured surfaces, and methods for regulating or "tuning" cellular adhesion at or on a substrate.

A number of difficulties can arise in the culturing of cells for implants from reaction with traditional supporting substrate materials or with their degradation products. For example, inflammatory reactions can occur in recipients due to the dissolving or absorption of some of the know substances, or because of reaction with decomposition products of some of the known substances (see: van der Gieben, *Circulation*, Volume 94, No. 7, 1996, which is incorporated herein by reference in its entirety). Furthermore, cracks and fractures can occur in the freshly cultured implant when the cultured implant is removed from the supporting substrate, if cultured cells bind too tightly to the supporting substrate due to its basic surface pore structure, or a pore structure that arises from dissolution of the supporting substrate. Such cracks are particularly problematic upon removal of cultured blood vessel implants from the supporting substrate, and constitute an important aspect in the production of vascular implants. Cracks, for instance, can be anchoring points for cellular and biomacromolecular attachment or serve as guiding motifs, giving rise to or triggering increased development of thrombi in recipients or patients, and for other deposits proteins, macrophages, and the like) that can become a risk for the recipients or patients after implantation.

Behavior with respect to bacteria and proteins that are deposited on the surfaces of the supporting substrate is also a factor affecting the successful culturing of implant cells, because bacteria and protein deposits can lead to significant inflammation in patients and to other problems with the growth and culture of the cells. In one aspect, for example, when an artificial substrate surface comes into contact with blood or any other biological fluids, a complex immune response is set into motion. For example, blood, urine, saliva, spinal fluids, and synovial fluids contain a wide variety of soluble proteins and other macromolecules of biological origin, which adsorb onto the introduced material to form a complex adsorbate layer. The composition and structure of this adsorbate layer largely can be determined by the varying affinities of the proteins and macromolecules towards the substrate. The subsequent cellular response is modulated through this adsorbate layer and may trigger adverse events such as the activation of the blood coagulation cascade. Associated complications may include acute or subacute thrombus formation, the initiation of inflammatory processes aided by bacterial infiltration and growth, accompanying biofilm formation, implant obstruction or occlusion through mineral encrustation, fatty deposit or calcified plaque formation, implant encapsulation or rejection, formation of myxoid tissue, scar formation, and necrosis.

Accordingly, in one aspect, this disclosure provides for a method of regulating cellular adhesion at or on a substrate, the method comprising:
a) contacting at least a portion of a substrate with at least one adhesion promoter to provide a treated substrate;
b) contacting the treated substrate with a solution comprising a known concentration of at least one polyphosphazene; and
c) removing the solvent from the polyphosphazene solution in contact with the treated substrate to provide a polyphosphazene micro-structured substrate;
d) observing the degree of cellular adhesion at the polyphosphazene micro-structured substrate; and
either
e) adjusting the degree of cellular adhesion at the polyphosphazene micro-structured substrate relative to that obtained in step c) by:
i) increasing or decreasing the polyphosphazene film height (film thickness) of the polyphosphazene micro-structured substrate;
ii) increasing or decreasing the size or aspect ratio of the structural element (pore), that is, increasing or decreasing the height/lateral dimension ratio of the structural elements of the polyphosphazene micro-structured substrate;
iii) increasing or decreasing the spatial density of (distance between) the structural elements of the polyphosphazene micro-structured substrate; or
iv) any combination thereof.
or
f) maintaining the degree of cellular adhesion at the polyphosphazene micro-structured substrate by preserving the polyphosphazene micro-structure on the substrate as provided in step c).

Step a) of this process is an optional step; thus, a substrate that has been untreated with an adhesion promoter also can be contacted with a polyphosphazene to provide a polyphosphazene micro-structured substrate. As used herein, the term contacting is intended to include any type of contacting, examples of which include, but are not limited to, coating, blending, mixing, compounding, fusing, washing, dipping, and the like, and other methods known to the art. Further, increasing or decreasing the aspect ratio refers to increasing or decreasing height/lateral dimension ratio of the structural element.

In another aspect, regulating cellular adhesion at a substrate can be carried out by adjustments in the polyphosphazene micro-structure on the substrate by the selection of the substrate material itself in view of the particular polyphosphazene matrix to be fabricated on that substrate. By way of example, regulating cellular adhesion at a substrate can include such substrate material design selections as follows:
a) selecting an inherently cellular adhesive material and using the polyphosphazene matrix as an additional controlling element for adjusting cellular adhesion, for example, to maximize or moderate cellular adhesion effects;
b) selecting an inherently cellular repulsive material in combination with the deposited polyphosphazene matrix as an additional controlling element for adjusting cellular adhesion, for example, to maximize or moderate cellular repulsion effects; or
c) selecting any combination thereof to achieve the desired cellular response.

It is to be understood that tailoring the cellular adhesive behavior at a substrate or cellular response of any type on the basis of the substrate-polyphosphazene combination can be accomplished at selected domains or regions of a particular substrate, using techniques such as masking methods that are well understood by one or ordinary skill. It is also to be understood that the cellular adhesive behavior of selected domains or regions of a particular substrate can tailored by, for example, contacting selected portions of a substrate with at least one adhesion promoter to provide a treated substrate, followed by contacting the larger substrate containing treated and untreated portions with at least one polyphosphazene.

In a further aspect, regulating cellular adhesion at a substrate can be carried out by adjustments in the polyphosphazene micro-structure itself on the substrate. For example, increasing the polyphosphazene micro-structure on the substrate, and hence decreasing cellular attraction, can be effected by:
a) increasing the polyphosphazene concentration in the polyphosphazene solution used to contact the substrate or treated substrate, as compared to a known polyphosphazene concentration;
b) repeating the steps of contacting the treated substrate with a solution comprising a known concentration of at least one polyphosphazene; and removing the solvent from the polyphosphazene solution in contact with the substrate or treated substrate to provide a polyphosphazene micro-structured substrate; or
c) a combination thereof.

In this aspect, for example, increasing the polyphosphazene concentration in the polyphosphazene solution used to contact the substrate or treated substrate can have the effect of: a) increasing the film height; b) decreasing the pore size; c) decreasing the spatial density of pores; d) increasing the aspect ratio of pores (structural elements), in which the pore depth becomes larger and the lateral size smaller; or e) any combination of these effects. While not intending to be bound by theory, it is thought that increasing the polyphosphazene concentration above a certain threshold will provide these effects, where this threshold concentration is related to or given by the inverse of the intrinsic viscosity (dilute, semi-dilute, concentrated regimes) and termed overlap concentration. Similarly, decreasing the polyphosphazene coating concentration below the threshold concentration affords the inverse of the effects a) through d) of this paragraph. Moreover, and while not intending to be theory-bound, using lower polyphosphazene concentration in the polyphosphazene solution used to contact the substrate or treated substrate can result in there being insufficient polymeric material on the surface to form a closed film, which may result in a dewetting instability on the substrate surface, resulting in an in situ reordering of the polyphosphazene film during formation and/or crystallization, thereby leading to the formation of the polyphosphazene domains (islets), in contrast to the bare, exposed substrate (pores). Thus, decreasing the polyphosphazene micro-structure on the substrate and hence increasing cellular attraction can be effected, for example, by decreasing the polyphosphazene concentration in the polyphosphazene solution used to contact the substrate or treated substrate.

These and other aspects and embodiments are provided in more detail in the Detailed Description section of this disclosure.

DETAILED DESCRIPTION OF THE INVENTION

Figure 1:
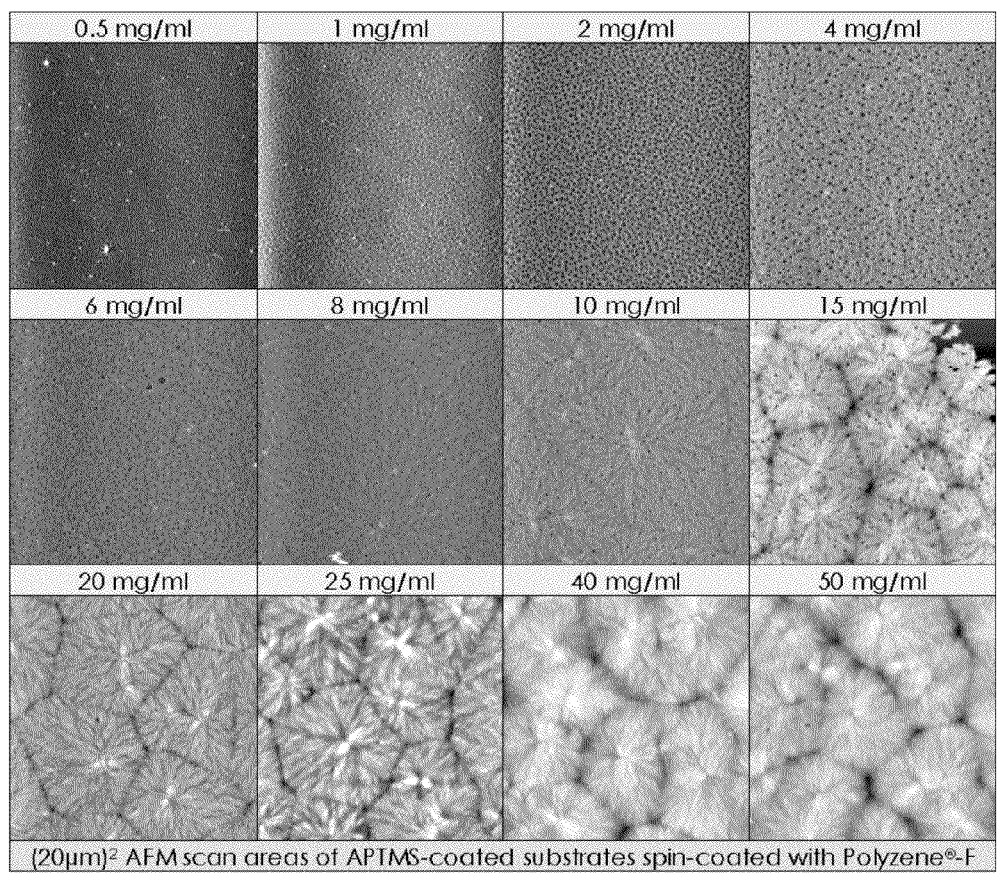
FIG. 1 presents Atomic Force Microscopy (AFM) images of the poly[bis(2,2,2-trifluoroethoxy)phosphazene] (Polyzene®-F) film morphology, using poly[bis(2,2,2-trifluoroethoxy)phosphazene] having a molecular weight of about $14.7 \times 10^6$ g/mol, illustrating one aspect of the films of this disclosure.
Figure 2:
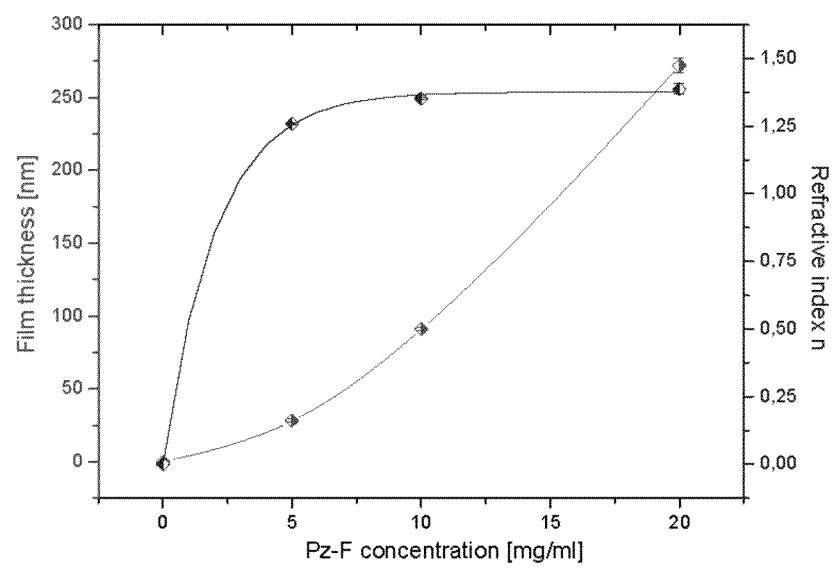
FIG. 2 is a plot of refractive index and film thickness versus spin-coating solution concentration of the poly[bis(2,2,2-trifluoroethoxy)phosphazene] (Polyzene®-F) films.

The present disclosure is drawn to a system for producing implants from biological materials that allows for highly selective growth of the desired cells and to assuring essentially damage-free separation of implants made of the desired cells from the supporting substrate.

In one aspect, the system for producing implants from biological materials includes regulating the extent or degree of cellular adhesion or repulsion at a substrate that is being used to culture cells for the implant. In one aspect, for example, this disclosure provides method of regulating cellular adhesion at a substrate or to a substrate, the method comprising:

a) contacting at least a portion of a substrate with at least one adhesion promoter to provide a treated substrate;
b) contacting the treated substrate with a solution comprising a known concentration of at least one polyphosphazene; and
c) removing the solvent from the polyphosphazene solution in contact with the treated substrate to provide a polyphosphazene micro-structured substrate;
d) observing the degree of cellular adhesion at the polyphosphazene micro-structured substrate; and
either
e) adjusting the degree of cellular adhesion at the polyphosphazene micro-structured substrate relative to that obtained in step c) by:
 i) increasing or decreasing the polyphosphazene film height (film thickness) of the polyphosphazene micro-structured substrate;
 ii) increasing or decreasing the size or aspect ratio of the structural element, that is, increasing or decreasing the height/lateral dimension ratio of the structural elements of the polyphosphazene micro-structured substrate;
 iii) increasing or decreasing the spatial density of (distance between) the structural elements of the polyphosphazene micro-structured substrate; or
 iv) any combination thereof.
or
f) maintaining the degree of cellular adhesion at the polyphosphazene micro-structured substrate by preserving the polyphosphazene micro-structure on the substrate as provided in step c).

Step a) of this method of regulating cellular adhesion at a substrate is an optional step; thus, a substrate that has been untreated with an adhesion promoter also can be contacted with a polyphosphazene to provide a polyphosphazene micro-structured substrate. Further, if the degree of cellular adhesion at the polyphosphazene micro-structured substrate is known beforehand, the process of regulating cellular adhesion can be altered accordingly. In this aspect, this disclosure provides method of regulating cellular adhesion at a substrate or to a substrate, the method comprising:

a) contacting at least a portion of a substrate with at least one adhesion promoter to provide a treated substrate;
b) contacting the treated substrate with a solution comprising a known concentration of at least one polyphosphazene; and
c) removing the solvent from the polyphosphazene solution in contact with the treated substrate to provide a polyphosphazene micro-structured substrate; and
e) controlling the degree of cellular adhesion at the polyphosphazene micro-structured substrate by:
 i) controlling the polyphosphazene film height (film thickness) of the polyphosphazene micro-structured substrate;
 ii) controlling the size or aspect ratio of the structural element, that is, increasing or decreasing the height/lateral dimension ratio of the structural elements of the polyphosphazene micro-structured substrate;
 iii) controlling the spatial density of (distance between) the structural elements of the polyphosphazene micro-structured substrate; or
 iv) any combination thereof.

The disclosed method of regulating cellular adhesion at a substrate can be carried out by adjustments in the degree of cellular adhesion at the polyphosphazene micro-structured substrate, as compared to a known degree of cellular adhesion on a substrate prepared using a known polyphosphazene concentration in the polyphosphazene solution. For example, increasing the polyphosphazene micro-structure on the substrate as outlined above can be carried out in a variety of ways, including:

a) increasing the polyphosphazene concentration in the polyphosphazene solution used to contact the treated substrate;
b) repeating steps c) and d) of claim 1 any number of times; or
c) a combination of a) and b).

Similarly, decreasing the polyphosphazene micro-structure on the substrate is effected by decreasing the polyphosphazene concentration in the polyphosphazene solution used to contact the treated substrate.

Further, the particular polyphosphazene can be used in combination with a particular biological material or biomacromolecules to tailor the micro-structure on the substrate and the cellular material produced therefrom. In this aspect, for example, a particular polyphosphazene can be used as a micro-structured masking area with known cellular modulations and modifying the substrate underneath by contacting the substrate with other solutions, such as solutions containing biomacromolecules known to have a specific affinity to the substrate material only. Alternately, this process can be carried out in a reverse fashion, that is, by using a particular polyphosphazene as a micro-structured specialized substrate and by contacting the material with solutions containing biomacromolecules with a specific affinity only for the polyphosphazene matrix.

In one aspect, the concentration of the polyphosphazene solution used to contact the substrate, whether treated or not, can be as low a concentration as desired, and can be up to about 200 mg per mL of solution if desired. Exemplary solvents for this process include various ketones, such as methyl ethyl ketone or acetone, esters such as ethyl acetate or butyl acetate, ethers such as THF, and also combinations thereof, including combinations with nonsolvents such as toluene, xylenes, and the like. In a further aspect, the concentration of the polyphosphazene solution used to contact the substrate, whether treated or not, can be up to about 150 mg per mL, up to about 125 mg per mL, up to about 100 mg per mL, up to about 75 mg per mL, up to about 50 mg per mL, up to about 35 mg per mL, to about 25 mg per mL, up to about 20 mg per mL, or up to about 15 mg per mL, up to about 10 mg per mL, up to about 5 mg per mL, up to about 2 mg per mL, up to about 1 mg per mL, or up to about 0.5 mg per mL, including any ranges or sub-ranges between these numbers. In a further aspect, solutions having a concentration derived from the inverse of the intrinsic viscosity of the polyphosphazene solutions, typically from about 0.5 to about 2.5 mg/mL, can be used.

Still a further aspect of this disclosure is a polyphosphazene micro-structured substrate having a polyphosphazene film thickness which can be up to about 1000 nm. Generally, as the polyphosphazene solution concentration is adjusted, the thickness of the resulting micro-structured surface is also adjusted, with higher concentrations providing thicker films. For example, the polyphosphazene micro-structured substrate prepared according to this disclosure can have a polyphosphazene film thickness up to about 1000 nm, up to about 750 mm, up to about 500 mm, up to about 400 mm, up to about 300 nm, up to about 200 nm, up to about 175 nm up to about 150 mm, up to about 125 nm, up to about 100 nm, up to about 75 nm, up to about 65 mm, up to about 60 nm, up to about 50 nm, up to about 40 nm, up to about 30 nm, up to about 20 nm, up to about 10 nm, up to about 5 nm, up to about 2 nm, or up to about 1 nm, including any ranges or sub-ranges between these numbers. In a further aspect, the polyphosphazene micro-structured substrate prepared according to this disclosure can have a lower limit polyphosphazene film thickness from about 1 nm, about 2 mm, about 3 n, about 4 n, or about 5 nm, up to any of the upper values disclosed. In one aspect, for the high molecular weight polyphosphazenes such as used in the Examples, polyphosphazene micro-structured substrates prepared according to this disclosure also can have a polyphosphazene film thickness from about 1 nm to about 300 nm.

When the polyphosphazene micro-structured substrate are prepared according to this disclosure, the spacing density of the void structure within the polyphosphazene micro-structured substrate can be from about 10,000 voids per 100 $\mu m^2$ to 0 voids per 100 $\mu m^2$, and any number between. In this aspect, for example, the spacing density of the void structure within the polyphosphazene micro-structured substrate prepared according to this disclosure can be from about 5,000-3,000 voids per 100 $\mu m^2$, from about 4,000-3,000 voids per 100 $\mu m^2$, from about 2,500-1,000 voids per 100 $\mu m^2$, from about 2, 200-900 voids per 100 $\mu m^2$, from about 1,000-600 voids per 100 $\mu m^2$, from about 700-200 voids per 100 $\mu m^2$, from about 500-200 voids per 100 $\mu m^2$, from about 400-100 voids per 100 $\mu m^2$, or from about 200-150 voids per 100 $\mu m^2$, including any ranges or sub-ranges between these numbers. Moreover, any of these numbers can be combined as a range of voids per 100 $\mu m^2$, for example, this disclosure is intended to include void structure spacing densities within the polyphosphazene micro-structured substrate of from about 5,000-3,000 voids per 100 $\mu m^2$, to about 200-150 voids per 100 $\mu m^2$, and ranges in between.

In a further aspect, when the polyphosphazene micro-structured substrate are prepared according to this disclosure, the polyphosphazene surface coverage of the polyphosphazene micro-structured substrate can be from near 0% to 100%, as surface coverage can be controlled along this continuum by the techniques disclosed herein. Particularly useful ranges include from about 25% to 100% and from 50% to 100% polyphosphazene surface coverage. In still another aspect, the polyphosphazene surface coverage of the polyphosphazene micro-structured substrate prepared according to this disclosure can be from about 50% to 100%, from about 75% to about 90%, from about 85% to about 95%, from about 90% to about 98%, from about 92% to about 97%, or from about 97% to about 97.5%, including any ranges or sub-ranges between these numbers.

In a further aspect of this disclosure, increasing the polyphosphazene micro-structure on the substrate and hence decreasing cellular adhesion and increasing cellular repulsion, can be effected by: a) increasing the polyphosphazene concentration in the polyphosphazene coating solution; b) increasing the polyphosphazene film thickness; c) decreasing the lateral spacing density of the void structure within the polyphosphazene micro-structured substrate per unit surface area; d) decreasing the average polyphosphazene-free pore size; e) increasing the substrate surface area covered by the polyphosphazene; or f) any combination thereof. Similarly, in this aspect, decreasing the polyphosphazene micro-structure on the substrate and hence increasing cellular adhesion and decreasing cellular repulsion, can be effected by: a) decreasing the polyphosphazene concentration in the polyphosphazene coating solution; b) decreasing the polyphosphazene film thickness; c) increasing the lateral spacing density of the void structure within the polyphosphazene micro-structured substrate per unit surface area; d) increasing the average polyphosphazene-free pore size; e) decreasing the substrate surface area covered by the polyphosphazene; or f) any combination thereof.

Polyphosphazenes

In one aspect, this disclosure provides the use of a substrate with a "forming" or form-building surface, that contains at least in part a polyphosphazene as a matrix for producing biological material that can be implanted in a mammal. In one aspect, for example, this disclosure provides the use of a substrate with a form-building surface, that contains at least in part a polyphosphazene having the following formula:

(I)

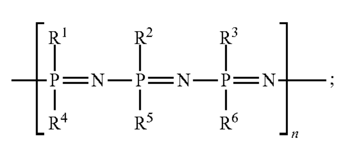

wherein n is 2 to ∞; and $R^1$ to $R^6$ are each selected independently from alkyl, aminoalkyl, haloalkyl, thioalkyl, thioaryl, alkoxy, haloalkoxy, aryloxy, haloaryloxy, alkylthiolate, arylthiolate, alkylsulfonyl, alkylamino, dialkylamino, heterocycloalkyl comprising one or more heteroatoms selected from nitrogen, oxygen, sulfur, phosphorus, or a combination thereof, or heteroaryl comprising one or more heteroatoms selected from nitrogen, oxygen, sulfur, phosphorus, or a combination thereof.

By indicating that n can be as large as ∞ in formula A, it is intended to specify values of n that encompass polyphosphazene polymers that can have an average molecular weight of up to about 75 million Daltons. For example, in one aspect, n can vary from about 40 to about 100,000. In another aspect, by indicating that n can be as large as ∞ in formula I, it is intended to specify values of n can be from about 4,000 to about 50,000, from about 7,000 to about 40,000, or from about 13,000 to about 30,000. In a further aspect, the degree of polymerization (n) of the biocompatible polymer according to Formula (I) is typically in a range of about 20 to about 200,000, and generally from about 40 to about 100,000.

In another aspect of this disclosure, the polyphosphazene used to prepare the micro-structured surfaces can have a molecular weight based on the above formula, which can be a molecular weight of at least about 70,000 g/mol, a molecular weight of at least about 1,000,000 g/mol, or a molecular weight from at least about $3 \times 10^6$ g/mol to about $20 \times 10^6$ g/mol. In another aspect, the polyphosphazenes can have a molecular weight of at least about 10,000,000 g/mol.

In a further aspect of the polyphosphazene formula (I) and the definitions of $R^1$ to $R^6$, the pendant side groups or moieties (also termed "residues") $R^1$ to $R^6$ are each independently variable and therefore can be the same or different. Further, $R^1$ to $R^6$ can be substituted or unsubstituted. The alkyl groups or moieties within the alkoxy, alkylsulfonyl, dialkylamino, and other alkyl-containing groups can be, for example, straight or branched chain alkyl groups having from 1 to 20 carbon atoms, typically from 1 to 12 carbon atoms, it being possible for the alkyl groups to be further substituted, for example, by at least one halogen atom, such as a fluorine atom or other functional group such as those noted for the $R^1$ to $R^6$ groups above. For example, by specifying alkyl groups such as propyl or butyl, it is intended to encompass any isomer of the particular alkyl group.

The alkyl groups in the alkoxy, alkylsulfonyl, dialkylamino, and any other alkyl-containing groups are, for example, straight-chain or branched-chain alkyl groups with 1 to 20 carbon atoms, wherein the alkyl groups can be, for example, substituted by at least one halogen atom, such as a fluorine atom. The 1 to 20 carbon atom, straight-chain or branched-chain description is also applicable to alkadiyl-type moieties such as aminoalkyl (amino-substituted alkyl groups) that can constitute $R^1$ to $R^6$.

In one aspect, examples of alkoxy groups include, but are not limited to, methoxy, ethoxy, propoxy, and butoxy groups, and the like, any of which can be substituted. For example, any alkoxy group can be substituted by one or more halogen atoms, such as fluorine atoms. One example of a suitable alkoxy group is the 2,2,2-trifluoroethoxy moiety. Thus, suitable alkoxy groups are OR groups in which R is any alkyl as defined herein. Thus, one one aspect, one or more of the alkoxy groups can contain at least one fluorine atom. Further, the alkoxy group can contain at least two fluorine atoms or the alkoxy group can contain three fluorine atoms. Certain alkoxy groups, such as iso-propyl and t-butyl, can contain six fluorine atoms. Alkoxy groups of the polymer can also be employed in combinations with other groups, including other variously substituted alkoxy groups. For example, combinations of alkoxy groups can be used, wherein one or more fluorine atoms are present on the polyphosphazene in combination with other groups or other substituent atoms.

Examples of alkylsulfonyl substituents include, but are not limited to, methylsulfonyl, ethylsulfonyl, propylsulfonyl, and butylsulfonyl groups.

Examples of dialkylamino substituents include, but are not limited to, dimethylamino, diethylamino, dipropylamino, and dibutylamino groups. Again, by specifying alkyl groups such as propyl or butyl, it is intended to encompass any isomer of the particular alkyl group.

An aryl group, for example as occurring in the aryloxy group can be, for example, a compound with one or more aromatic ring systems, in which the aryl group can be unsubstituted or substituted with one or more alkyl groups, one or more halogens, one or more alkoxy groups, one or more amino groups, or any combination thereof. Examples of aryl groups are phenyl, naphthyl, and substituted analogs thereof. In one aspect, for example, aryl groups in this disclosure can be substituted or unsubstituted and can have from 6 to about 20 carbon atoms. Accordingly, examples of aryloxy groups include, but are not limited to, phenoxy and naphthoxy groups, and substituted analogs or derivatives thereof including, for example, substituted phenoxy and naphthoxy groups.

The heterocycloalkyl group can be, for example, a ring system which contains from 3 to 10 atoms, or from 3 to 7 atoms, at least one ring atom being a nitrogen, oxygen, sulfur, phosphorus, or any combination of these heteroatoms. The hetereocycloalkyl group can be substituted, for example, by one or more alkyl, alkoxy, halide, or other substituent. Examples of heterocycloalkyl groups include, but are not limited to, imidazoline, imidazolidine, piperidinyl, piperazinyl, pyrrolidinyl, and morpholinyl groups, and substituted analogs thereof.

The heteroaryl group can be, for example, a compound having one or more aromatic ring systems, at least one ring atom being a nitrogen, an oxygen, a sulfur, a phosphorus, or any combination of these heteroatoms. The heteroaryl group can be substituted for example by one or more alkyl, alkoxy, halide, or other substituent. Examples of heteroaryl groups include, but are not limited to, imidazolyl, thiophene, furane, oxazolyl, pyrrolyl, pyridinyl, pyridinolyl, isoquinolinyl, and quinolinyl groups, and derivatives thereof, such as substituted groups.

In one aspect, this disclosure provides the use of a substrate with a "forming" or form-building surface, that contains at least in part the polyphosphazene, poly[bis(2,2,2-trifluoroethoxy)phosphazene] (also referred to further herein as poly [bis(trifluoroethoxy)-phosphazene]), or a derivative or analog thereof, as a matrix for producing biological material that can be implanted in a mammal. The polymer poly[bis(2,2,2-trifluoroethoxy)phosphazene] or derivatives thereof as disclosed herein, have chemical and biological qualities that distinguish this polymer from other know polymers in general, and from other know polyphosphazenes in particular. In a further aspect, the polyphosphazene can be derivatives of poly[bis(2,2,2-trifluoroethoxy) phosphazene], such as other alkoxide, halogenated alkoxide, or fluorinated alkoxide substituted analogs thereof.

In one aspect, the poly[bis(trifluoroethoxy)phosphazene] polymer can be made up of repeating monomers represented by formula (I), wherein $R^1$ to $R^6$ are all trifluoroethoxy ($OCH_2CF_3$) groups, and wherein n may vary from at least about 40 to about 100,000, as disclosed herein. Alternatively, one may use derivatives of this polymer as described herein.

The term "derivatives" is meant to refer to polymers made up of monomers having the structure of formula I but where one or more of the $R^1$ to $R^6$ functional group(s) is replaced by a different functional group(s), such as an unsubstituted alkoxide, a halogenated alkoxide, a fluorinated alkoxide, or any combination thereof, or where one or more of the $R^1$ to $R^6$ is replaced by any of the other functional group(s) disclosed herein, but where the biological inertness of the polymer is not substantially altered.

In one aspect of the polyphosphazene of formula (I) illustrated above, for example, at least one of the substituents $R^1$ to $R^6$ can be an unsubstituted alkoxy substituent, such as methoxy ($OCH_3$), ethoxy ($OCH_2CH_3$) or n-propoxy ($OCH_2CH_2CH_3$). In another aspect, for example, at least one of the substituents $R^1$ to $R^6$ is an alkoxy group substituted with at least one fluorine atom. Examples of useful fluorine-substituted alkoxy groups $R^1$ to $R^6$ include, but are not limited to $OCF_3$, $OCH_2CF_3$, $OCH_2CH_2CF_3$, $OCH_2CF_2CF_3$, $OCH(CF_3)_2$, $OCCH_3(CF_3)_2$, $OCH_2CF_2CF_2CF_3$, $OCH_2(CF_2)_3CF_3$, $OCH_2(CF_2)_4CF_3$, $OCH_2(CF_2)_5CF_3$, $OCH_2(CF_2)_6CF_3$, $OCH_2(CF_2)_7CF_3$, $OCH_2CF_2CHF_2$, $OCH_2CF_2CF_2CHF_2$, $OCH_2(CF_2)_3CHF_2$, $OCH_2(CF_2)_4CHF_2$, $OCH_{12}(CF_2)_5CHF_2$, $OCH_2(CF_2)_6CHF_2$, $OCH_2(CF_2)_7CHF_2$, and the like. Thus, while trifluoroethoxy ($OCH_2CF_3$) groups are particularly useful in some aspects, these further exemplary functional groups also may be used alone, in combination with trifluoroethoxy, or in combination with each other. In one aspect, examples of especially useful fluorinated alkoxide functional groups that may be used include, but are not limited to, 2,2,3,3,3-pentafluoropropyloxy ($OCH_2CF_2CF_3$), 2,2,2,2',2',2'-hexafluoroisopropyloxy ($OCH(CF_3)_2$), 2,2,3,3,4,4,4-heptafluorobutyloxy ($OCH_2CF_2CF_2CF_3$), 3,3,4,4,5,5,6,6,7,7,8,8,8-tridecafluorooctyloxy ($OCH_2(CF_2)_7CF_3$), 2,2,3,3,-tetrafluoropropyloxy ($OCH_2CF_2CHF_2$), 2,2,3,3,4,4-hexafluorobutyloxy ($OCH_{12}CF_2CF_2CHF_2$), 3,3,4,4,5,5,6,6,7,7,8,8-dodecafluorooctyloxy ($OCH_2(CF_2)_7CHF_2$), and the like, including combinations thereof.

Further, in some aspects, 1% or less of the $R^1$ to $R^6$ groups may be alkenoxy groups, a feature that may assist in crosslinking to provide a more elastomeric phosphazene polymer. In this aspect, alkenoxy groups include, but are not limited to, $OCH_2CH=CH_2$, $OCH_2CH_2CH=CH_2$, allylphenoxy groups, and the like, including combinations thereof. Also in formula (I) illustrated herein, the residues $R^1$ to $R^6$ are each independently variable and therefore can be the same or different.

Typically, at least one of the groups $R^1$ to $R^6$ in the polymer used is an alkoxy group, substituted with at least one fluorine atom.

Substrates

In one particular aspect of this disclosure, the biocompatible polymer according to Formula (I) is provided as a coating on the substrate to develop the forming surface. In this aspect, there is no particular limitation on the substrate used, and it can be any material, such as a plastic, a polymer or co-polymer, a rubber material, a metal, a metal alloy, a ceramic, an elastomer, an elastomeric membrane, a fabric, a polysaccharide, a glass, or any combination thereof, such as a composite. Moreover, there is no particular limitation on the shape or the size of the substrate. For example, the substrate can be in the form of an object of any desired shape, a surface, a sheet, a mesh, a tube, a tearable material, a scaffold, a perforated material, a sphere, a polyhedron, a surface with raised areas, and the like. The biocompatible coating has, for example, a thickness from about 1 nm up to about 1000 μm, from about 1 nm up to about 10 μm, and from about 1 nm up to about 1 μm. In another aspect, the substrate having a forming surface is a shaped object or molding or molded article made of the biocompatible material according to formula (I).

Adhesion Promoters

In another aspect of this disclosure, an intermediate layer that contains an adhesion promoter, a the layer, or a transitional material is placed between the surface of the substrate and the biocompatible coating that contains a polyphosphazene compound or derivative. The adhesion promoter may improve the adhesion of the coating to the surface of the substrate by coupling of the adhesion promoter to the surface of the substrate through ionic and/or covalent bonds, for example, and by further coupling of the adhesion promoter to the described polymer of formula (I) of the coating, for instance, through ionic and/or covalent bonds. In this aspect, depending on the nature of the substrate and its intended application, a substrate first may be cleaned if desired, for example, by ultrasonication or by immersing the substrate material into various liquid chemical cleaning baths, solutions, or reagents, followed by rinsing with an appropriate solvent based on the particular cleaning bath. Examples of cleaning reagents include, but are not limited to, oxidizing, acidic, or alkaline etching solutions. After several such cleaning steps, substrates then may be immersed in solutions containing a surface reactive adhesion promoter, for a time period sufficient to afford the desired mono- or multilayers of the adhesion promoter on the substrate. Typically, excess, unreacted reagents may be removed by further cleaning, which can be followed by a final drying step.

In one aspect, the adhesion promoter can comprise an acid component and an amine component. The acid component and the amine component can be situated in different substances, materials, or molecules, or within a single substance, material, or molecule. For example, the orientation of the adhesion promoter components relative to the substrate and the phosphazene polymer may be represented generally by the connectivity: substrate-acid component-amine component-polyphosphazene. In this aspect, the acid component can comprise any moiety that provides an acid functionality and can be selected from, for example, acids, esters thereof partial esters thereof, or acid halides, which form hydroxyl ($OH^-$) groups upon hydrolysis with water. Examples of materials that provide acid components include, but are not limited to, carboxylic acids, phosphoric or phosphonic acid derivatives, sulfuric or sulfonic acid derivatives, orthosilic acid derivatives, boronic acid derivatives, titanic acid derivatives, and all other known species, compounds, compositions, mixtures, or moieties that are known to form $OH^-$ groups upon hydrolysis with water. In this aspect, the linkage with the amine (or amidine) component may be established by, for example, a typical amide linkage which results from the reaction of the acid component with the free amine and subsequent dehydration. In another aspect, the amide linkage also may be established with the elimination of halide groups instead of hydroxyl, when the acid component comprises an acid halide. While not intending to be bound by theory, the substrate-acid component linkage itself may established by ether formation or hydrogen bonding, or by any method by which the acid moiety or component may interact effectively with the substrate. In another aspect, for example, amino acids are useful as adhesion promoters and provide prototypical examples of molecules in which the acid component and the amine component are situated within a single molecule.

Further to this aspect, the adhesion promoter or spacer can contain a polar end-group, examples of which include, but are not limited to, hydroxy, carboxy, carboxyl, amino, nitro groups, and the like. Further, end groups can be selected from alkoxy, alkylsulfonyl, dialkylamino, aryloxy, heterocycloalkyl having nitrogen as a hetero atom, or heteroaryl having nitrogen as a hetero atom, any of which having up to about 20 carbon atoms, and any of which can be variously substituted, for instance by halogen atoms such as chlorine or fluorine. In this aspect, fluorine-substituted polar end groups work well. The adhesion promoter can, for example, be an amino-terminated silane or one based on aminosilane, amino-terminated alkenes, nitro-terminated alkenes and silanes, or an alkylphosphonic acid.

In one aspect, aminoalkyltrialkoxysilanes such as aminopropyltrialkoxysilanes work well as adhesion promoters when used in combination with polyphosphazenes, examples of which include compounds according to formulas II and III, illustrated here.

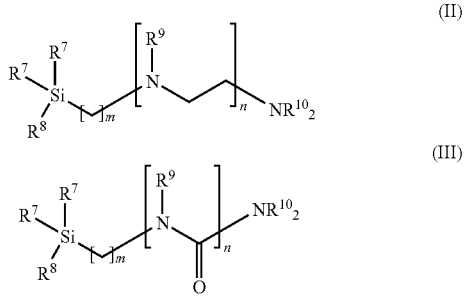

In formulas II and III, $R^7$ can be selected independently from —O(alkyl), —O(alkyl) ester, or alkyl; $R^8$ can be selected independently from —O(alkyl); $R^9$ can be selected independently from H or alkyl; and $R^{10}$ can be selected independently from H or alkyl, wherein alkyl is defined herein, and wherein at least one of $R^7$ or $R^9$ comprises a hydrolyzable —O(alkyl) group. Because at least one of $R^7$ or $R^8$ comprises a hydrolyzable group, a hydrolysis reaction can occur to form a covalent surface grafting. In formulas II and III, m can be an integer from 0 to about 20, and m is typically an integer from 2 to 12, with m being 3 being typical. Also in formulas II and III, n can be an integer from 0 to 4, with n typically being selected from 1 or 2. In one aspect, $R^9$ and $R^{10}$ can both be H, or in another aspect, $R^9$ and $R^{10}$ can both be $CH_3$, wherein m is 3 and n is either 1 or 2. While not intending to be bound by theory, it is believed that pendant groups of the siloxane adhesion promoter that have a positive dipole or quadrupole moment, whether temporary or permanent, create a favorable interaction with the negatively polarized fluorinated pendant groups of the polyphosphazene, including fluorinated alkoxide groups such as trifluoroethoxy. For example, pendant groups such as dimethylacetamido, trimethylureido, pentafluorophenyl, quaternary amines, ternary, secondary, primary amines and alkylated amides and the like, exhibit favorable adhesion.

In another aspect of this disclosure, the adhesion promoter can be an organosilicon compound, such as an amino-terminated silane, or based on aminosilane, amino-terminated alkenes, nitro-terminated alkenes, and silanes, or an alkylphosphonic acid. Concerning the various silane-based adhesion promoters, these can include ureido- and glycidyl-terminated silanes which are especially useful for bonding of epoxy resins, thiol or acroyl termini which can be employed for bonding to vinylogous and acrylate based rubbers, or other substrates disclosed herein. For fluoroelastomers, amine and perfluoro based silanes are generally used. Other examples of silane-based adhesion promoters include N-(2-aminoethyl)-3-aminopropyl-trimethoxysilane, bis[(3-trimethoxysilyl)propyl]-ethylene diamine, and other commercially-available functional silane reagents. In one aspect, a particularly useful silane-based adhesion promoter is (3-aminopropyl)trimethoxysilane (APTMS).

In various other aspects, an exemplary compound with a pentafluorophenyl pendant group can include the following compound of formula IV, which exhibits favorable silanole end groups, and in which $R^7$ and $R^8$ are the same as their definition for formulas II and III.

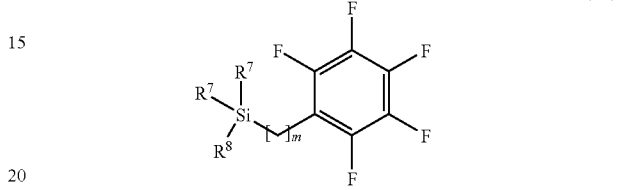

Thus, in formula IV, $R^7$ can be selected independently from —O(alkyl), —O(alkyl) ester, or alkyl; $R^8$ can be selected independently from —O(alkyl); wherein alkyl is defined herein, and wherein at least one of $R^7$ or $R^8$ comprises a hydrolyzable —O(alkyl) group.

A comparison of the respective hydrolysis rates for the analogous —O(alkyl) series of adhesion promoters that differ only by $R^7$ and $R^8$, wherein $R^7$ and $R^8$ are selected from OMe, OEt, or OPr, reveals a decreasing hydrolysis rate as one progresses from OMe to OPr. For example, an $(OMe)_3$-terminated silane will hydrolyze 70 times faster than an $(OEt)_3$ endcapped silane in acidified aqueous methanol. Therefore the choice of silane end groups can be adapted to meet desired reaction times. Unless slower reaction times are desired, $(OMe)_3$-substituted silanes are very useful and are typically used.

A further aspect of the disclosure is provided by additional silane adhesion promoters, that are suitable for a gas-phase deposition processes, examples of which are provided as formulas V and VI.

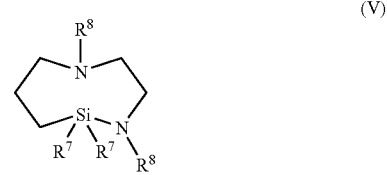

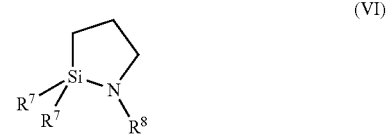

For example, in formulas V and VI, $R^7$ can be selected from —O(alkyl) or alkyl; and $R^8$ can be selected from H or alkyl. Adhesion promoters of formulas V and VI, are suited for both liquid phase and gas phase silane deposition methods, regardless of whether the environment is aqueous or anhydrous. Thus, in one aspect, these adhesion promoters do not need to hydrolyze before being able to react with a hydroxyl rich surface. For example, and while not intending to be bound by theory, formulas V or VI may initiate a ring-opening sequence by reacting with surface bound hydroxyl groups immediately on contact to yield the open-chain variants. Further, reactions rates of the adhesion promoters are convenient. As described herein, such surface modifications may be performed in liquid phase, using etchants, oxidizing solutions, volatile solvents and other reactive species. Moreover, this method employing the adhesion promoters affords a homogeneous and smooth deposition of the adhesion promoter, and film thicknesses also will depend on the concentration and deposition time of the adhesion promoter.

Biological Material

The term "biological material" includes, for example, eucaryotic cells, monolayer or multilayer cellular aggregations, tissues, or cell components of mammals, especially of human origin. In one aspect, the donor of the biological starting material is identical to the recipient of the implantable biological material. Examples of the biological starting material or biological material include endothelial cells of various origins (for example, from skin, foreskin, blood vessels such as the aorta, fatty tissues, eye, omentum, umbilical cord, varices, or the like), epithelial cells of various origins (for example, from the stomach, intestine, or the like), bone cells, cartilage cells, and all adherent cells or cells in which adherence is inducible, cell aggregations or tissues (for example, artificial cultured skin or similar tissue), natural tissues, proteins, sugar molecules and lipids. Artificial organs, blood vessels, bones, cartilage, myelin sheaths, and the like, can be produced by using the substrate with a forming surface, as disclosed herein.

A further aspect of the present disclosure concerns a process for producing the substrates with forming surface as defined above; wherein the application of a coating of the biocompatible polymer according to Formula (I) to the surface of a shaping body, molding (or molded article) or supporting substrate is known from the prior art.

In a further aspect, for example, the substrate with a forming surface can be produced according to the following general procedure.

(a) A solution containing at least one compound of the general Formula (I) at a concentration of 0.1%-99% is prepared, typically in a polar organic solvent. Ethyl acetate, various other ketones, acetone, THF, toluene, or xylenes, for example, can be used here as solvents. Mixtures of these solvents are also usable, or they can be supplemented by other solvents. This solution is applied to a substrate that exhibits little if any adhesion to the polymer, such as glass, silicon, various ceramics or other appropriate materials such as polymers (PDMS, Teflon, PMMA, polycarbonate or silicone). The surfaces of the substrates listed can also be chemically modified, for instance, by introducing certain functional groups (—$NH_2$, —OH, —COOH, —COH, —COOMe, —$CF_3$, and the like).

(b) Evaporation of the solvent can proceed without further measures; but in the best case the concentration of the solvent vapor over the substrate is controlled, as are the pressure and the temperature. At the beginning of the first phase of drying, the atmosphere over the coated substrate should be saturated with solvent vapor, with the concentration of the solvent vapor then being reduced slowly over many hours. The temperature can vary from −30° C. to +90° C. The pressure can follow a gradient from normal pressure to water aspirator vacuum (20 Torr) during the first phase of drying. After the first phase of drying, the coated substrate is further dried for a certain period at oil pump vacuum (0.1 Torr).

The substrate coated with the biocompatible polymer according to Formula (I) can then be used directly, without or after appropriate sterilization. Various coating thicknesses from about 0.1 µm to about 300 µm or even thicker, from about 0.5 µm to about 30 µm, from about 1 µm to about 10 µm, or from about 2 µm to about 7 µm can be obtained, depending on the concentration of the polymer solution and the conditions used during the first phase of drying.

Another aspect of this disclosure concerns a substrate with a micro-structured surface comprising at least partly a biocompatible polymer according to Formula (I) as defined above, with the size or magnitude of the surface structures being in the range of nanometers, micrometers, or even larger or smaller, generally in the range of 10 nm to 100 µm. In one aspect, the biocompatible polymer is present on the substrate as a coating with an externally micro-structured surface.

The structuring of the surface is not subject to any particular limitation. For instance, all structures that can be generated photolithographically, with an electron beam, with an ion beam with a laser, or by other techniques, can be produced. The microstructuring of the surface of the substrate or of the coating can also be obtained by "fusion structuring or melt structuring", in which a thin wire is brought to the melting temperature of the biocompatible polymer and then melts the desired structure into the surface of the coating by direct contact.

Special advantages can be attained by means of this structuring with structures that affect the flow behavior of liquids particularly favorably (for example, sharkskin or lotus effect) imprinted into the surface of the coating or substrate.

Cellular Growth on Micro-Structured Surfaces

One aspect of this disclosure provides a method for the gradual adjustment or tuning of the cellular response to a polyphosphazene micro-structured substrate, from a cellular adhesion and proliferation response regime to a cellular repulsion regime. In one aspect, such a tailored response can be obtained on the basis of the selected phosphazene microstructure size range, for example, the size, concentration, and structures of the pores of the polyphosphazene coating. These structural features of the pores can depend from, among other things, the concentrations of the polyphosphazene-containing solution used to contact the substrate. Generally, at higher polyphosphazene concentrations, the cellular repulsion regime can be accessed, as evidenced by elongated structures of the cellular motile mode. However, at lower polyphosphazene concentrations, including uncoated substrates, a cellular adhesion and proliferation response regime can be accessed, as evidenced by the reduction of cellular spreading and reduced cell motility.

Moreover, a continuum of intermediate regimes or types of cellular proliferation and growth can be accessed with the methods of this disclosure. For example, an intermediate regime of moderate cellular attraction can be obtained, from moderate attraction to moderate repulsion, which can be obtained on the basis of the decrease of spacing density of the void structure within the polyphosphazene micro-structure, and thus the effective surface coverage of the polyphosphazene micro-structure. In addition, desired cellular response can be correlated with the polyphosphazene surface coverage and the spacing density of the structural element (such as pores), both of which can be related to the polyphosphazene film thickness and adjusted or tuned by the polyphosphazene coating solution concentration. Thus, lower polyphosphazene concentrations provide lower surface coverage and lower film thickness, along with a higher spacing density of the structural element, and results in greater cellular attraction. Similarly, higher polyphosphazene concentrations provide higher surface coverage and greater film thickness, along with a lower spacing density of the structural element, all resulting in greater cellular repulsion.

Accordingly, cellular attraction to an adhesion promoter-treated surface can be obtained by Polyzene®-F surface coverage of from about 74% to about 88.5% and any range in between, a spacing density of the pore structural element of from about 2150 per 100 µm$^2$ to about 950 per 100 µm$^2$, and a Polyzene®-F film thickness of from 0 to about 20 nm. In contrast, cellular repulsion at an adhesion promoter-treated surface can be obtained by Polyzene®-F surface coverage of from about 97% and higher, for example from 97% to about 97.5%, a spacing density of the pore structural element of from about 200 per 100 µm$^2$ to about 150 per 100 µm$^2$, and a Polyzene®-F film thickness of from about 175 nm to about 290 nm. A continuum of cellular responses from moderate attraction to moderate repulsion can be obtained at intermediate values. Thus, the introduction of nanometer sized voids, for example, from about 10 nm up to about 0.5 µm-sized voids as structural elements in the polyphosphazene micro-structure, enables the cells to attach to the underlying substrate, the spacing density of which controls the cellular attachment behavior. The average pore size diameter is from about 75 nm to about 150 nm.

In a further aspect of the disclosure, for specific cell growth applications, the target substrate material, the optional adhesion promoter layer and the micro-structured polyphosphazene coating (and/or combinations and permutations thereof may specifically be chosen to create a blend or a gradient implant superstructure, which favorably combines and/or mixes the desired cellular response properties of base substrate material, adhesion promoter layer and polyphosphazene coating, in order to achieve a targeted or selective cellular response. For example a combination of cellular adhesion, cellular growth, cellular proliferation, and cellular differentiation on the newly formed implant surface may be obtained with such a blend or gradient implant superstructure. Such a combination is not limited to physical (cellular) perception only, but may also include the formation of chemically contrasted structures, that is, containing an inherent, spatially-resolved, selectivity or affinity for a variety of chemical, biological, and/or pharmaceutical agents to further enhance the desired biological and cellular response. For instance, as illustrated in Example 2, a gradual decrease of cellular adhesion and cell spreading on such a gradient structure can be obtained, where a purely cell-adhesive APTMS surface is gradually converted into a cellular-repulsive surface by applying a polyphosphazene micro-structuring technique and coating.

In another aspect of this disclosure, Table 2 of Example 2 summarizes some examples of coating and structural parameters that can be used to attain a desired cellular response on a micro-structured substrate. General information on the cellular repulsive behavior arising from thick poly[bis(2,2,2-trifluoroethoxy)phosphazene] films (typically >1 µm range) for particular cell lines, are illustrated as follows: SK-N-BE (2c) human neuroblastoma cell line (see Eric Barrett et al., Biomacromolecules 2005, May-June, 6(3), pp. 1689-97); L929 mouse fibroblasts, hepatoma cell line HepG2 (see Alexander Welle, J. Biomater. Sci. Polymer Edn. 2004, Vol. 15, No. 3, pp. 357-3700; HeLa cells, cervical cancer cell line (see Yoshi Hori et al., Artificial Organs, 26(10):868-893 (2002)); and thrombocytes, erythrocytes and *E. coli* (Dr. Claudia Gries, Dissertation, University of Heidelberg, 2001). Other aspects of this disclosure are provided in Cato T. Laurencin, et al., Journal of Biomedical Materials Research, Vol. 27, 963-973 (1993). Each of these references is incorporated herein by reference in their entireties.

The present disclosure is further supported and illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present disclosure or the scope of the appended claims.

Unless indicated otherwise, temperature is reported in degrees Centigrade and pressure is at or near atmospheric. An example of the preparation of a polyphosphazene of this disclosure is provided with the synthesis of poly[bis(trifluoroethoxy)phosphazene] (PzF) polymer, which may be prepared according to U.S. Patent Application Publication No. 2003/0157142, the entirety of which is hereby incorporated by reference. Other disclosures of phosphazene syntheses are provided in S. V. Vinogradova, D. R. Tur, and V. A. Vasnev, *Russian Chemical Reviews*, vol. 67(6), 515-534 (1998) (translated from *Uspekhi Khimii* vol 67(6), 573-594 (1998)), which is incorporated by reference in its entirety. Accordingly, any polyphosphazene encompassed in this disclosure and having $R^1$ through $R^6$ as defined herein, can be prepared according to the of phosphazene synthesis methods disclosed in, for example, the Vinogradova et al. publication. In additional, the synthetic procedures by which the polyphosphazenes employed in this disclosure can be made also are disclosed in Allcock, Harry R., "Poly(organophosphazenes)-Unusual New High Polymers," Angew. Chem. Int. Ed. Engl. 16, 147-156 (1977); and in Allcock, Harry R., "Chemistry and Applications of Polyphosphazenes," Wiley-Interscience (2002) (ISBN-10: 0471443719; ISBN-13: 978-0471443711); both of which are incorporated herein by reference in their entireties.

Also unless indicated otherwise, when a range of any type is disclosed or claimed, for example a range of molecular weights, layer thicknesses, concentrations, temperatures, and the like, it is intended to disclose or claim individually each possible number that such a range could reasonably encompass, including any sub-ranges encompassed therein. For example, when the Applicants disclose or claim a chemical moiety having a certain number of atoms, for example carbon atoms, Applicants' intent is to disclose or claim individually every possible number that such a range could encompass, consistent with the disclosure herein. Thus, by the disclosure that an alkyl substituent or group can have from 1 to 20 carbon atoms, Applicants intent is to recite that the alkyl group have 1, 2, 3, 4, 5, 6, 7, 8, 9, 10, 11, 12, 13, 14, 15, 16, 17, 18, 19, or 20 carbon atoms. In another example, by the disclosure that the particular spacing density of a structural element can be from 200 to 150 voids/100 µm$^2$, Applicants include within this disclosure the recitation that the particular spacing density of a structural element can be approximately 200 voids/100 µm$^2$, approximately 190 voids/100 µm$^2$, approximately 180 voids/100 µm$^2$, approximately 170 voids/100 µm$^2$, approximately 160 voids/100 µm$^2$, and/or approximately 150 voids/100 µm$^2$, including any range or sub-range encompassed therein. Accordingly, Applicants reserve the right to proviso out or exclude any individual members of such a group, including any sub-ranges or combinations of sub-ranges within the group, that can be claimed according to a range or in any similar manner, if for any reason Applicants choose to claim less than the full measure of the disclosure, for example, to account for a reference that Applicants are unaware of at the time of the filing of the application.

All publications, patents, and documents mentioned in the disclosure are, in relevant part, incorporated herein by reference in their entireties, for the purpose of describing and disclosing, for example, the constructs and methodologies that are described in the publications, which might be used in connection with the presently described process and apparatus. The publications discussed above and throughout the text are provided solely for their disclosure prior to the filing date of the present application. Nothing herein is to be construed as an admission that the inventors are not entitled to antedate such disclosure by virtue of prior invention. Should the usage or terminology used in any reference that is incorporated by reference conflict with the usage or terminology used in this disclosure, the usage and terminology of this disclosure controls. The Abstract of the disclosure is provided herewith to satisfy the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." The Abstract is not intended to be used to construe the scope of the appended claims or to limit the scope of the subject matter disclosed herein. Any use of the past tense to describe an example otherwise indicated as constructive or prophetic is not intended to reflect that the constructive or prophetic example has actually been carried out.

EXAMPLES

The following Examples provide, among other things, experimental evidence for the measurable effect of polyphosphazene surface structure dimensions on cell proliferation and growth. Examples are provided for the preparation of micro-structured polyphosphazene coatings, and for cell proliferation and growth on target surfaces prepared according this disclosure. Examples will also show that, within the spatial range, aspect ratio, and size or magnitude (lateral and height dimensions) of the polyphosphazene micro-structures, the cellular response can be gradually turned from a cellular adhesion and proliferation regime to one of cellular repulsion, the targeted cellular response of which will be depending on the designed and selected phosphazene micro-structure size range.

Example 1

Preparation of Micro-Structured Polyphosphazene Coatings

Example 1a

Substrate Preparation: Cleaning Protocol

Sample glass substrates having the dimensions 20 mm×20 mm×0.1 mm were pre-cleaned with Caro's acid [($H_2SO_4$ (96%): $H_2O_2$ (30%) in a 3:1 (v/v) ratio)] for a period of 30 minutes, rinsed with copious amounts of ultrapure water, and dried under a stream of Argon to afford chemically clean substrate surfaces.

Example 1b

Substrate Preparation: Adhesion Promoter Deposition Protocol

The cleaned glass substrates from Example 1a were used in this procedure. The protocol of Stenger et al. (D. A. Stenger, J. H. Georger, C. S. Dulcey, J. J. Hickman, A. S. Rudolph, T. B. Nielsen, S. M. McCort, and J. M. Calvert, *J. Am. Chem. Soc.* vol. 114, 8435-8442, (1992)) was used for the deposition of an adhesion promoter, as is described for aminopropyltrimethoxysilane [APTMS, $(MeO)_3SiCH_2CH_2CH_2NH_2$]. A stock "silanization" solution of 500 mL of 95% methanol and 5% ultrapure water (v:v) was acidified by adding 29 µL of glacial acetic acid, which aids in the hydrolysis of the silane. Once the APTMS solution was prepared, 1 part per volume of the 3-aminopropyltrimethoxysilane was added to 99 parts per volume of this APTMS solution.

Previously cleaned glass substrates were immersed in this solution and maintained or "incubated" for a period of 2 h. After incubation, samples were subjected to ultrasonication in absolute methanol for 10 min, removed and rinsed with pure methanol, and blown dry under a Stream of argon. The resulting aminopropylsiloxane multilayers were cured or crosslinked by drying in an oven for 1 h at 105° C., then allowed to cool to ambient temperature. After cooling, samples were stored under argon until further used.

Example 1c

Substrate Coating: Preparation of Micro-Structured Polyphosphazene Coatings

The APTMS-coated glass slides prepared according to Example 1b were spin-coated with poly[bis(2,2,2-trifluoroethoxy)phosphazene] (Polyzene®-F) having a molecular weight of about $14.7 \times 10^6$ g/mol, which corresponds to a degree of polymerization based on formula I of n=60,500. This sample of poly[bis(2,2,2-trifiluoroethoxy)phosphazene] was characterized by $^1H$ NMR, $^{13}C$ NMR, $^{31}P$ NMR, Infrared (IR) spectroscopy, viscosimetry, and GPC analysis. Spin-coating was carried out using Polyzene®-F solutions ranging in concentration of about 0.5-20 mg/mL in methylisobutylketone, at a speed of about 3000 rpm for a period of 60 seconds. This coating procedure provided Polyzene®-F coatings ranging in thickness from about 1 nm up to about 0.5 µm, and having a decreasing gradient of a heterogeneous substrate-film open-cell porous micro-structure. Coatings ranging in thickness from about 1 nm up to about 0.5 µm can be prepared using this technique by adjusting variables such as spin rate and time, Polyzene®-F solution concentration, and the like, as understood by one of ordinary skill in the art. Poly[bis(2, 2,2-trifluoroethoxy)phosphazene] (Polyzene®-F) is described in formula I, in which each of $R^1$ through $R^6$ is 2,2,2-trifluoroethoxy (—$OCH_2CF_3$). As understood by one of ordinary skill, the molecular weight of about $13 \times 10^6$ g/mol used for this Polyzene®-F coating can be an indicator of the film thickness that can be achieved in this coating process.

Example 1d

Characterization of Micro-Structured Polyphosphazene Coatings

The micro-structured polyphosphazene coatings prepared according to Example 1c were characterized to study the effect of surface micro-structure and film dimensions on cell attachment, proliferation, and growth. Accordingly, films were characterized by Atomic Force Microscopy (AFM) and Optical Ellipsometry, to obtain correlating data for film thickness and film micro-structure morphology, as follows.

FIG. 1 illustrates a series of AFM images of the micro-structured polyphosphazene coatings prepared according to Example 1c, demonstrating the selective growth of a variety of Polyzene®-F film micro-structures on APTMS coated glass substrates, as a function of the spin-coating solution concentration. For example at lower concentrations, the Polyzene®-F film micro-structure morphologies span a range from explicitly open-cell, heterogeneous morphology, up to completely closed, spherulitic film structures produced at higher spin-coating solution concentrations. Similarly, film thickness, the number of open cell structures (pores), the dimensions of the open cell structures, the lateral spacing density of pores, and effective surface area covered by the Polyzene®-F film micro-structure are shown to correlate with the spin-coating concentration employed.

According to the data presented in FIG. 1, the most porous coating with the highest number of open cell structures occurs at the lowest concentration of 0.5 mg/mL spin-coating concentration. Between spin-coating solution concentrations of about 0.5 mg/mL and about 10 mg/mL, the layer growth is substantially two-dimensional in that increasingly greater coverage of the underlying substrate is achieved with higher concentrations, as seen by the darker color structure of each AFM image which represents domain boundaries. As observed at the 10 mg/mL concentration, the two-dimensional structure is substantially completely closed, and spherulitic film morphology is clearly seen at higher concentrations as three-dimensional growth dominates and increases the thickness of the film. Thus, at lower concentrations, a more porous and less continuous structure is formed and at higher concentrations, a less porous and more continuous structure is formed.

The Polyzene®-F micro-structured films prepared according to Example 1C were further evaluated with AFM and Optical Ellipsometry to assess the film thickness range and refractive index. These data are presented in Table 1.

TABLE 1

Polyzene ®-F film thickness and refractive index as a function of the spin-coating Polyzene ®-F solution concentration.

| Concentration | Thickness [nm] | | |
|---|---|---|---|
| [mg/mL] | AFM | Ellipsometry | Refractive Index |
| 4 | 25 ± 4 | 28 ± 1.2 | 1.258 ± 0.005 |
| 10 | 85 ± 12 | 91 ± 0.8 | 1.353 ± 0.003 |
| 20 | 287 ± 14 | 272 ± 5 | 1.387 ± 0.02 |

Error values of the AFM measurements presented in Table 1 were based on the root-mean-square roughness of the Polyzene®-F films. As illustrated, the different techniques used to measure thickness yielded comparable results. In addition, the ellipsometric measurements showed a clear increment in the refractive index as the film thickness increased.

These numeric findings supplement the micro-structure morphology information obtained with AFM. Surface morphologies obtained in Example 1c indicated a varying degree of porosity in the polymer films. As the refractive index reaches a value of n=1.39 (at ≥20/mg/mL Polyzene®-F concentration), the polymer film is becoming free of voids beyond this regime. Hence, the measured refractive index can be interpreted as the effective sum of the respective refractive indices of bulk Polyzene®-F polymer (n=1.39) and pure air (n=1). This information shows that the pores are open cell structures void of phosphazene polymer, exposing the APTMS substrate underneath. Therefore, the higher the concentration of the polymer in the spin-coating solution, the closer the index of refraction of the coating to that of the polymer itself is observed.

Figure 3:
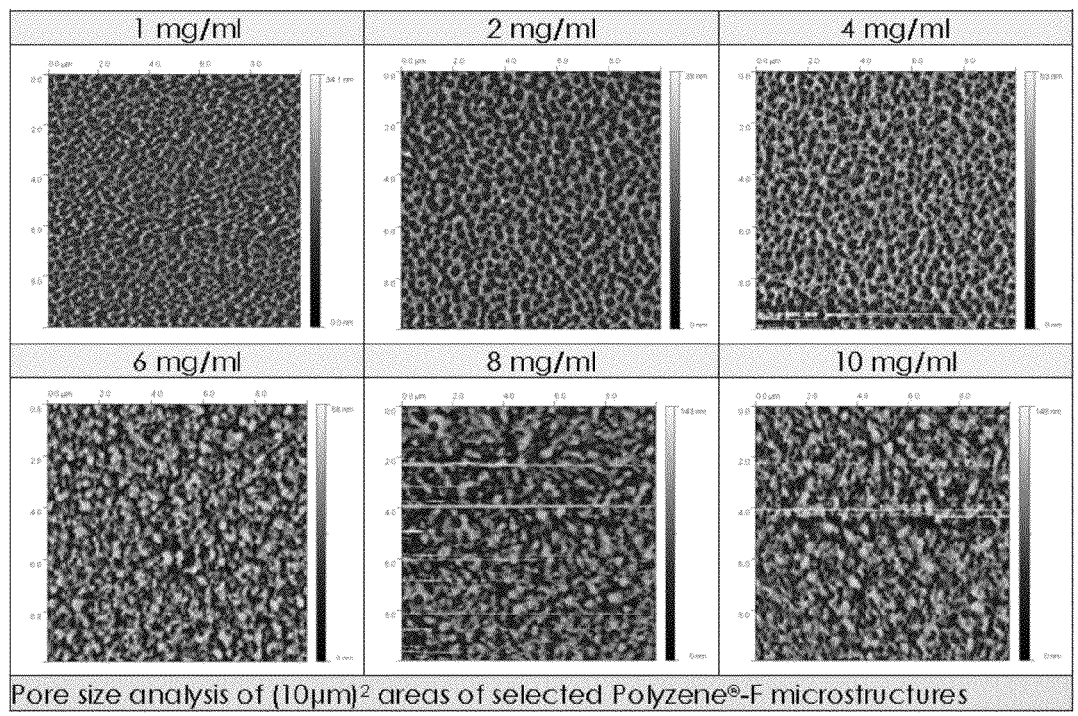
FIG. 3 illustrates a pore size analysis of selected microstructures obtained by leveling and normalizing AFM images of the Polyzene®-F spin-coated according to Example 1c. Pores are dark in color in FIG. 3, in contrast to the lighter color Polyzene®-F.
Figure 4:
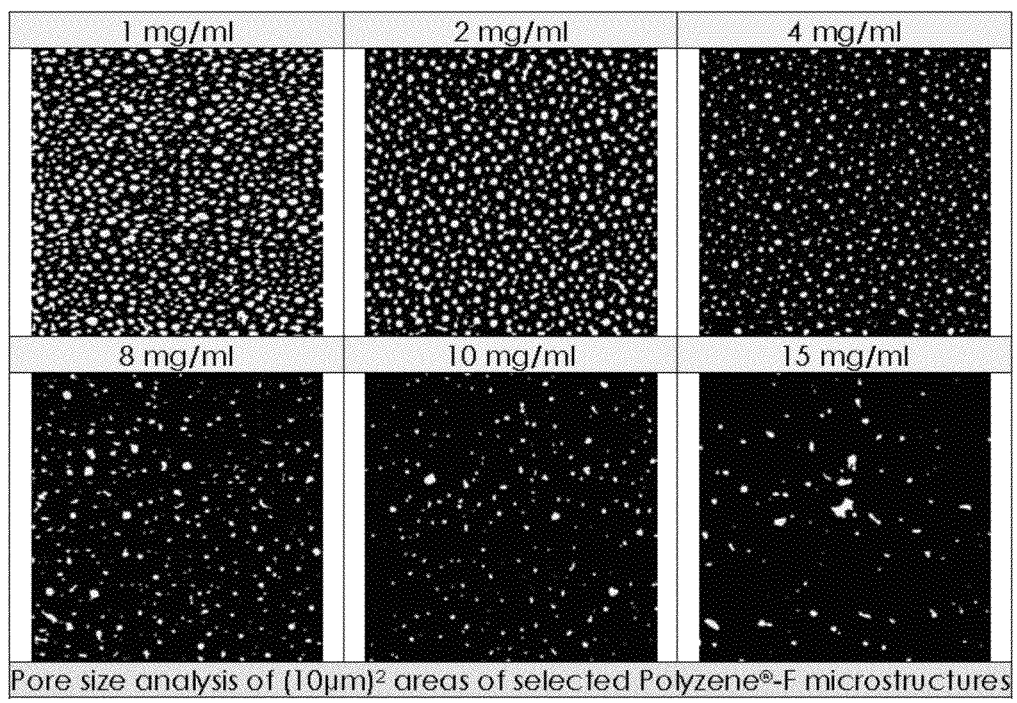
FIG. 4 illustrates a pore size analysis of selected microstructures obtained by leveling and normalizing AFM images of the Polyzene®-F spin-coated according to Example 1c, in which height level information was employed as a criterion to select the open cell (void) structures and images were converted into a masked area.

A pore size analysis also was conducted to further investigate the relative pore count and percentage of surface coverage obtained with the polyphosphazene micro-structuring technique of Example 1c. FIG. 3 illustrates a pore size analysis of selected micro-structures obtained by leveling (flattening) and normalizing the AFM images of the Polyzene®-F spin-coated according to Example 1c, using the open-source Gwyddion modular software for scanning probe microscopy data (such as AFM) visualization and analysis. In FIG. 3, pores are marked in red color (darker) in order to contrast these to the surrounding Polyzene®-F structure (lighter in color). Thus, AFM images were leveled and normalized in which height level information was employed as criterion to select the open cell (void) structures. These images were converted into a masked area as illustrated in FIG. 4 using the Gwyddion software, on which all further calculations were carried out using the original AFM image and height information data. Thus, FIG. 4 provides a pore frequency analysis of (10 μm)$^2$ areas of selected Polyzene®-F spin-coatings based on spin-coating solution concentrations, spacing density, and size information obtained from FIG. 3. In this aspect, a "grain" size analysis was conducted with Gwyddion in which the light-colored pores of FIG. 4, their spatial density, and their size, were analyzed. Thus, at 1 mg/mL a large number of pores can be observed, while at 15 mg/mL, a much smaller number of pores can be seen. Median pore size can be calculated for each image of FIG. 4.

Figure 5:
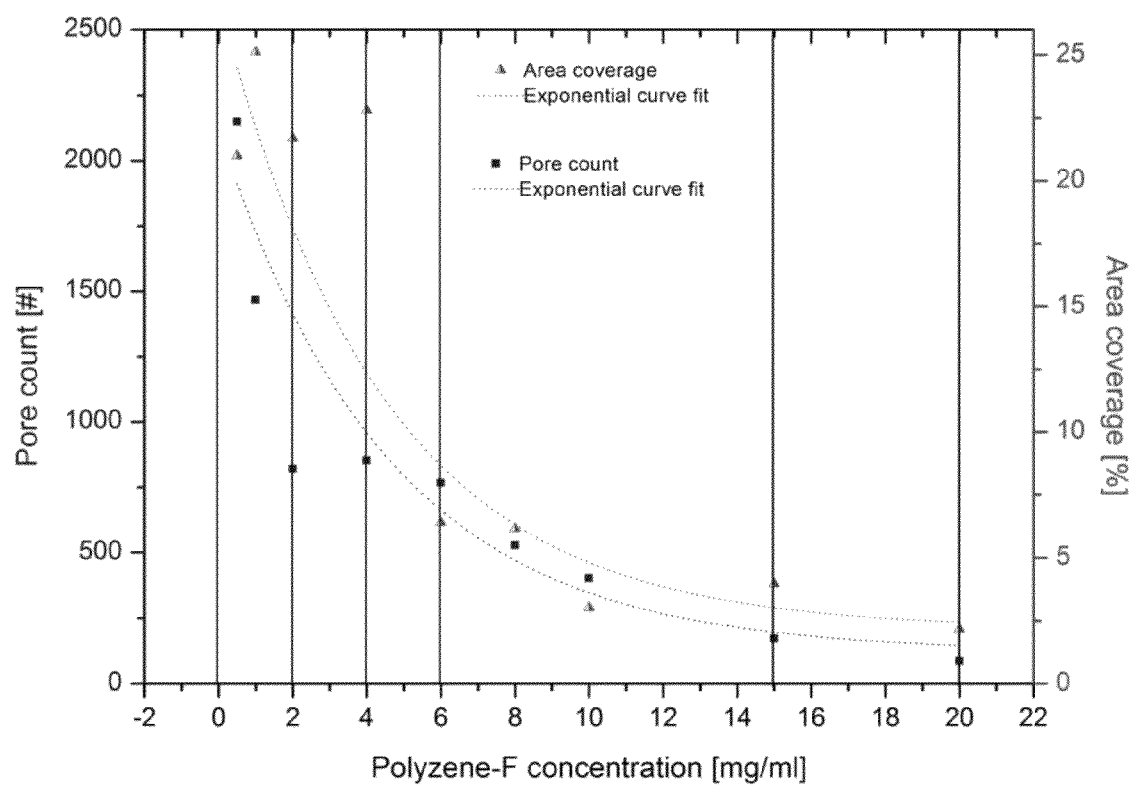
FIG. 5 illustrates a plot of pore count and percent (%) pore area (voids) covered on the substrate material per 100 μm² surface area, based on the data obtained in FIGS. 3 and 4.

FIG. 5 illustrates a plot of pore count and percent (%) pore area (voids) covered on the substrate material per 100 μm$^2$ surface area, based on the data obtained in FIG. 4 data as derived from the FIG. 3 data. Thus, both pore count as obtained from FIG. 4 and area coverage as calculated from the pore count of FIG. 4 are plotted in FIG. 5.

Accordingly, the following conclusions can be drawn from the information illustrated in FIGS. 1-5.

A) Within the boundaries of Example 1c, the polyphosphazene film thickness dimensions ranged from 0 nm to about 0.3 μm (300 nm). This range works well for the targeted tailoring of cellular adhesion to the micro-structured substrate, and can be achieved by altering the concentration of the Polyzene®-F spin-coating solution. The film deposition technique employed in Example 1c allows for the formation of even higher film thicknesses, for example up to about 10 μm or even up to 100 μm or greater, if higher polymer concentrations and other parameters are used. The film deposition technique employed in Example 1c also allows for tailoring the film thickness as desired with a substantial measure of control. Although there is no theoretical limit as to the upper boundary for film thickness, particularly desirable ranges are typically up to about 1 μm for the techniques described in this disclosure. Thus, the effective film thickness range that provides for modulation of cellular response by this structuring technique can be obtained according to this disclosure. The lateral film dimensions of the film are not limited by the deposition technique and the lateral substrate dimensions can easily exceed the centimeter range. Any suitable coating technique for the soluble polymer, as known to one of ordinary skill can be employed to coat a wide variety of substrates of varying sizes.

B) The open-cell porous polyphosphazene micro-structures created by using the micro-structuring technique of Example 1c afforded a lateral spacing density of from 0 pores up to about 2500 pores per 100 μm$^2$ surface area, having a pore size range of from 0 nm to about 0.5 μm in diameter. The average pore size range is typically in the range from about 75 to about 150 nm in diameter. The effective surface area covered by the polyphosphazene micro-structure, within the parameters described in Example 1c, ranged from approximately 74% to about 100% effective surface area covered.

Example 1e

Additional Substrates

Examples 1a and 1b of the present disclosure can be repeated using a variety of substrates. For example, a range of substrates may be employed according to this disclosure, including but not limited to, any plastic or polymeric material, any metal or metal alloys, or any ceramic material. Crystalline or non-crystalline substrate materials can be employed as well.

Example 1f

Additional Adhesion Promoters

Example 1b of the present disclosure also can be repeated using a variety of adhesion promoters. For example, a range of adhesion promoters with a polar end group may be employed, examples of which include but are not limited to hydroxy, carboxy, carboxyl, amino, or nitro end groups. Further, end groups can be selected from alkoxy, alkylsulfonyl, dialkylamino, aryloxy, heterocycloalkyl having nitrogen as a hetero atom, or heteroaryl having nitrogen as a hetero atom, any of which having up to about 20 carbon atoms, and any of which can be variously substituted, for instance by halogen atoms, including fluorine. The adhesion promoter can, for example, be an amino-terminated silane or one based on aminosilane, amino-terminated alkenes, nitro-terminated alkenes and silanes, or an alkylphosphonic acid.

In a further aspect, Example 1 can be carried out using APTMS-coated glass slides prepared according to Example 1b, which can be spin-coated with poly[bis(2,2,2-trifluoroethoxy)phosphazene] (Polyzene®-F) having a molecular weight ranging from about $12 \times 10^6$ g/mol to about $18 \times 10^6$ g/mol.

Example 2

Cell Proliferation and Growth on Target Surfaces

Example 2 demonstrates how that, within the lateral and height dimension ranges of the polyphosphazene micro-structures tailored and prepared according to Example 1, the cellular response to a polyphosphazene-micro-structured substrate can be gradually adjusted or tuned from a cellular adhesion and proliferation response regime to a cellular repulsion regime, in which the targeted cellular response depends upon the desired phosphazene micro-structure size range.

Figure 6:
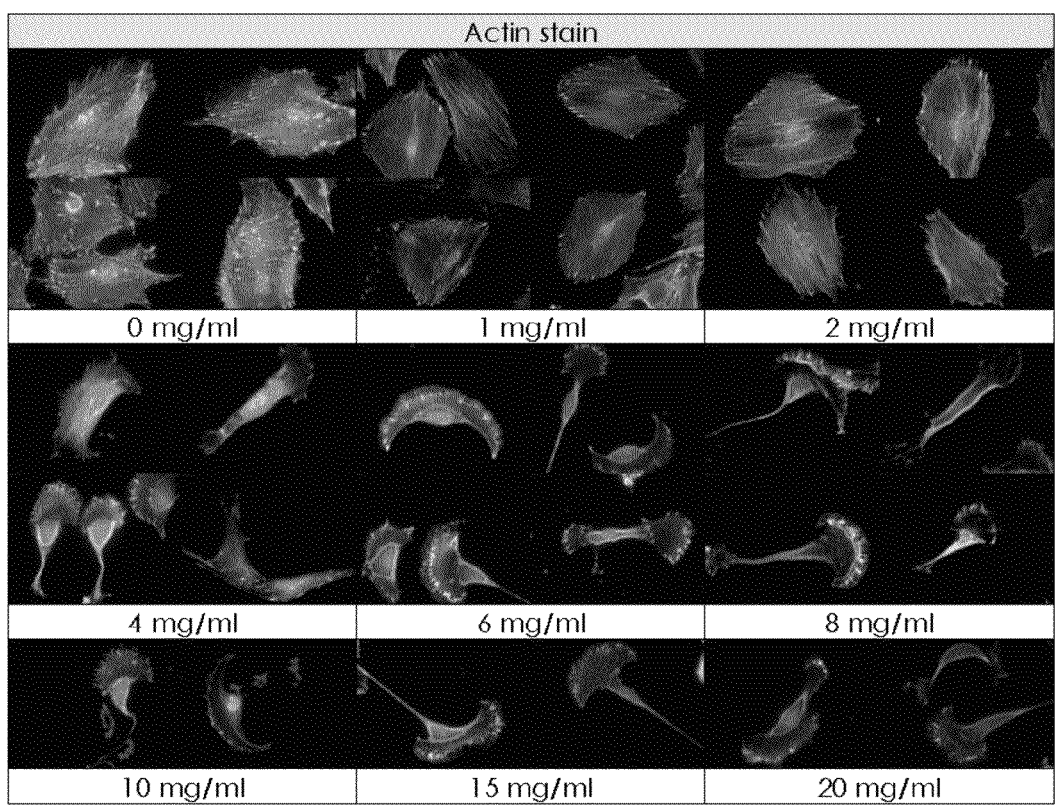
FIG. 6 illustrates a series of in vitro fibroblast cell adhesion studies on Polyzene®-F coated substrates, in which fibroblast cells exhibited a concentration-dependent adhesion behavior, as can be seen by the staining of the actin cytoskeleton.

This example relates to fibroblast cellular adhesion studies on Polyzene®-F coated substrates. Fibroblast cellular adhesion, proliferation and spreading were studied in an in vitro cell culture experiment on the surfaces prepared according to Example 1, in which it was observed that the fibroblast cells exhibited a concentration-dependent adhesion behavior. For a Polyzene®-F spin-coating solution concentration range of from 0 mg/mL to about 2 mg/mL Polyzene®-F, no concernible difference between coated and uncoated APTMS glass reference substrates was observed. Thus, as illustrated in FIG. 6, cells spread considerably as can be seen by the staining of the actin cytoskeleton. The formation of filopodia with focal adhesion points is clearly apparent in FIG. 6. In FIG. 6, a collection of 4 images is provided for each concentration from 0 mg/mL to 8 mg/mL, and a collection of 2 images is provided for each concentration from 10 mg/mL to 20 mg/mL. The red or brighter dots around the cells that are visible in the lower concentration images are the cellular fibropodia structures that serve to anchor the cell to the substrate. At higher concentrations, the elongated structures illustrate the motile mode in which the cells are searching for an location on which to anchor. Thus, in the range of from about 4 mg/mL to about 6 mg/mL Polyzene®-F, the cellular spreading is reduced considerably as compared to lower concentrations. Cells seem to show a rather motile phenotype which increases even further as the polymer concentration goes to and beyond 8 mg/mL Polyzene®-F. However, at these higher concentrations, the cell spreading was reduced, and it was observed that the cell motility was much smaller in comparison to the uncoated substrates.

Figure 7:
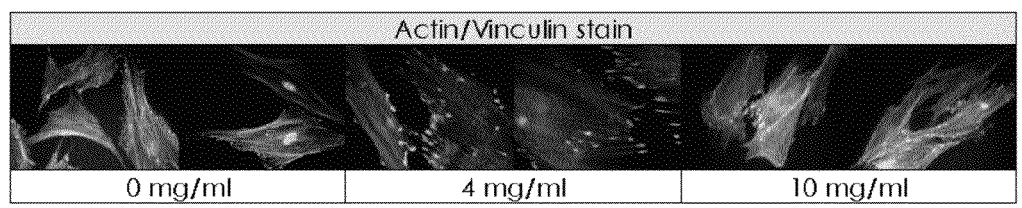
FIG. 7 illustrates a series of in vitro fibroblast cell adhesion studies on Polyzene®-F coated substrates similar to FIG. 6, in which fibroblast cells exhibited a concentration-dependent adhesion behavior. The FIG. 7 illustrations were obtained at somewhat higher magnification and using a different stain as compared to the FIG. 6 images.

FIG. 7 illustrates a similar series of in vitro fibroblast cell adhesion studies on Polyzene®-F coated substrates in which fibroblast cells exhibited a concentration-dependent adhesion behavior. The FIG. 7 illustrations were obtained at somewhat higher magnification and using a different stain as compared to the FIG. 6 images. In FIG. 7, the focal contact points are clearly visible in the 0 mg/mL image, whereas no focal contact points are visible in the 10 mg/mL image. Thus, from 0 mg/mL to about 4 mg/mL Polyzene®-F concentration, cells develop focal contacts quite readily, while at 10 mg/mL Polyzene®-F concentration, cellular adhesion appears to be stagnant.

The data from these figures illustrates that the threshold for the transition or change of cellular adhesion and proliferation behavior occurred between about 4 mg/mL and about 6 mg/mL Polyzene®-F, which corresponds to a Polyzene®-F film thickness of 20-65 nm. Below this threshold, cellular adhesion and proliferation behavior resembles that of the APTMS substrate, and fibroblast cells were found to spread.

An intermediate regime of moderate attraction was observed from about 65 nm up to about 175 nm, followed by an intermediate regime of moderate repulsion from about 175 nm to about 290 nm, which is related to the decrease of spacing density of the void structure within the polyphosphazene micro-structure, and thus the effective surface coverage thereof. As illustrated in the data in Table 2, the complete range of Polyzene®-F surface coverage is from about 74% to about 100% surface coverage, as shown in FIG. 5.

Above this threshold, the Polyzene®-F micro-structure is devoid of pores or voids and the Polyzene®-F film is clearly cell-repulsive, as shown in Table 2, and FIGS. 6 and 7.

TABLE 2

Summary of coating and structural parameters to attain a desired cellular response

| Coating Concentration [mg/mL] | Film Thickness [nm] | Spacing density of structural element | Polyzene ®-F surface coverage | Desired cellular response |
|---|---|---|---|---|
| 0-4 | 0-20 | 2150-950 voids/ 100 μm² | 74-88.5% | Cell attraction |
| 4-6 | 20-65 | 950-650 voids/ 100 μm² | 88.5-92.5% | Moderate attraction |
| 6-15 | 65-175 | 650-200 voids/ 100 μm² | 92.5-97% | Moderate repulsion |
| 15-20 | 175-290 | 200-150 voids/ 100 μm² | 97-97.5% | Cell repulsion |

These cellular adhesion and repulsion studies and how cellular adhesion and repulsion can be modulated, can be summarized in the data provided in Table 2, which summarizes data from the figures provided herein. For example, the surface coverage and the desired cellular response are extrapolated from FIG. 5. From about 0 nm to about 20 nm Polyzene®-F film thickness, cellular attraction and adhesion could be achieved. From about 20 nm to about 65 nm Polyzene®-F film thickness, moderate cellular attraction was achieved, while from about 65 nm to about 175 nm Polyzene®-F film thickness, moderate cellular repulsion can be achieved, and for a Polyzene®-F film thickness from about 175 nm to about 290 nm and beyond, cellular repulsion can be achieved.

The introduction of nanometer sized voids, for example, from about 10 nm up to about 0.5 µm-sized voids as structural elements in the polyphosphazene micro-structure, enables the cells to attach to the underlying substrate, the spacing density of which controls the cellular attachment behavior. The average pore size diameter is from about 75 nm to about 150 nm.

Full cellular repulsion is observed on completely closed, spherulitic domain structures substantially devoid of pores. In this case, the lateral domain size of the spherulites is in the about 10 µm to about 100 µm range.

On the basis of these data, it is concluded that the number of attached cells and their morphology depended on the coating concentration initially used for the preparation of the coated samples, and thus was directly related to the Polyzene®-F film thickness and micro-structure morphology, that is, the surface area covered by Polyzene®-F and the lateral spacing density of the pores.

Example 3

Cell Proliferation and Growth on Target Surfaces

Example 3 illustrates the effect of adhering a biologically active biomacromolecule with a specific selectivity towards Polyzene®-F to an otherwise cell-repulsive polyphosphazene micro-structure, to completely revert the cellular attachment and spreading behavior.

Figure 8:
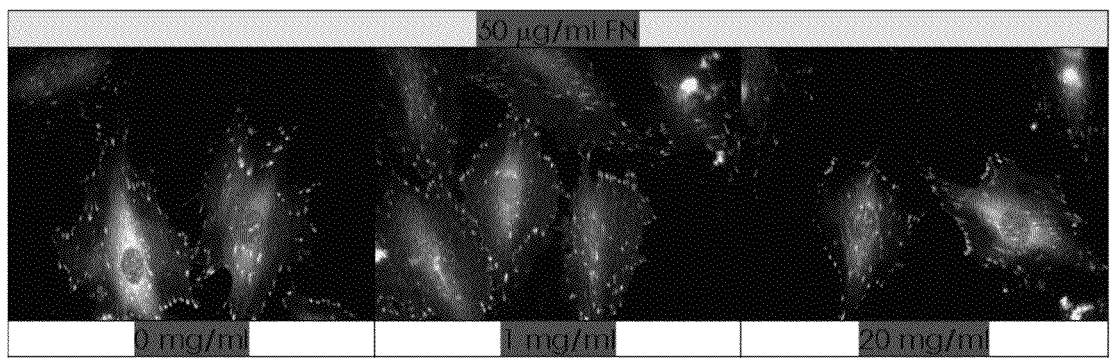
FIG. 8 illustrates the focal adhesion contacts on fibronectin (FN)— treated Polyzene®-F coated substrates.

Polyzene®-F coated substrates prepared according to Example 1 were pre-treated with a 50 µg/mL fibronectin (FN) solution to afford selective adsorption of the biologically active macromolecule. A cell seeding experiment analogous to that of Example 2 was repeated. The results of this study are illustrated in FIG. 8, where focal adhesion contacts on fibronectin (FN)-treated Polyzene®-F coated substrates can be observed. In comparison to the cell repulsive behavior observed with substrates that were created using greater than 2-4 mg/mL Polyzene®-F solutions, a complete reversal of the cell repulsive behavior was observed, FIG. 8.

We claim:

1. A substrate comprising a polyphosphazene micro-structured surface, wherein:
    a) the polyphosphazene micro-structured substrate has a polyphosphazene film thickness from 65 nm to 290 nm;
    b) the spacing density of the void structure within the polyphosphazene micro-structured substrate is from 650 voids per 100 µm$^2$ to 100 voids/100 µm$^2$; and
    c) the surface coverage of the polyphosphazene micro-structured substrate is from 92.5% to 97.5%, and
    d) the polyphosphazene is present in the polyphosphazene film at a concentration from about 6 mg/mL to about 20 mg/mL,
  wherein the substrate is selected from the group consisting of a polymer, a copolymer, a rubber material, an elastomer, an elastomeric membrane, a fabric, a polysaccharide, a glass, and combinations thereof, and
  wherein the substrate exhibits cellular repulsion.

* * * * *